United States Patent
Dax et al.

(10) Patent No.: US 6,201,025 B1
(45) Date of Patent: Mar. 13, 2001

(54) N-ARALKYLAMINOTETRALINS AS LIGANDS FOR THE NEUROPEPTIDE Y Y5 RECEPTOR

(75) Inventors: Scott L. Dax, Landenberg, PA (US); Timothy W. Lovenberg, San Diego, CA (US); Ellen W. Baxter, Glenside, PA (US); John R. Carson, Norristown, PA (US); Donald W. Ludovici, Quakertown, PA (US); Mark A. Youngman, Warminster, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/413,292

(22) Filed: Oct. 6, 1999

Related U.S. Application Data

(60) Provisional application No. 60/103,446, filed on Oct. 7, 1998.

(51) Int. Cl.⁷ .................. A61K 31/135; C07C 211/00
(52) U.S. Cl. .......................................... 514/657; 564/428
(58) Field of Search ................ 514/657; 564/428

(56) References Cited

U.S. PATENT DOCUMENTS

| 5,286,747 | * | 2/1994 | Arvidsson et al. | 514/481 |
| 5,594,034 | * | 1/1997 | Gidda et al. | 514/657 |

FOREIGN PATENT DOCUMENTS

| 0 064 964 | 11/1982 | (EP) . |
| 0 334 538 | 9/1989 | (EP) . |
| 97/20822 | 6/1997 | (WO) . |

OTHER PUBLICATIONS

A. M. Johansson et al. Resolved cis–and trans –2–Amino–5–methoxy–1–methyltetralins, J. Med Chem, vol. 30, No. 4, 1987, pp. 602–611.

C.H. Lin et al. Centrally Acting Serotonergic Agents J. Med. Chem. vol. 36, No. 6 1993, pp. 671–682, Tables I, II.

A.M. Johansson et al. Novel Dopamine Receptor Agonists and Antagonists with Preferential Action on Autoreceptors, J. Med. Chem., vol. 28, No. 8, 1985, pp. 1049–1053: See P. 1050: compound 6.

* cited by examiner

*Primary Examiner*—Deborah C. Lambkin
(74) *Attorney, Agent, or Firm*—Ralph R. Palo

(57) ABSTRACT

β-Aminotetralin derivatives of the formula:

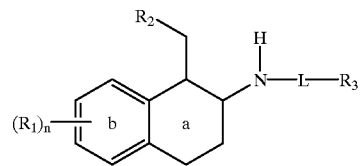

(I)

which are ligands for the neuropeptide Y Y5 (NPY5) receptor, methods of preparation and pharmaceutical compositions containing a β-aminotetralin derivative as the active ingredient are described. The 62-aminotetralins are useful in the treatment of disorders and diseases associated with NPY receptor subtype Y5.

16 Claims, No Drawings

N-ARALKYLAMINOTETRALINS AS LIGANDS FOR THE NEUROPEPTIDE Y Y5 RECEPTOR

This application is a Provisional Application No. 60/103,446 filed Oct. 7, 1998.

FIELD OF THE INVENTION

This invention relates to a series of β-aminotetralin derivatives, pharmaceutical compositions containing them and intermediates used in their preparation. The compounds of the invention are ligands for the neuropeptide Y Y5 (NPY5) receptor, a receptor which is associated with a number of central nervous system disorders and affective conditions.

BACKGROUND OF THE INVENTION

Regulation and function of the mammalian central nervous system is governed by a series of interdependent receptors, neurons, neurotransmitters, and proteins. The neurons play a vital role in this system, for, when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to humans, neuropeptides have been discovered in a number of animal species. In some instances the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein which is enzymatically processed to yield the active substance. Based upon these differences, compared to small molecule neurotransmitters, neuropeptide-based strategies may offer novel therapies for CNS diseases and disorders. Specifically, agents that affect the binding of neuropeptides to their respective receptors or ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders and diseases have been treated with small molecules and peptides which modulate neuronal responses to endogenous neurotransmitters.

One example of the class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY, which is primarily synthesized by endocrine cells in the gut, and pancreatic polypeptide, which is synthesized by the pancreas. Neuropeptide Y is a single peptide protein that consists of thirty-six amino acids containing an amidated C-terminus. Like other members of the pancreatic polypeptide family, NPY has a distinctive conformation that consists of an N-terminal polyproline helical region and an amphiphilic-helix joined by a characteristic PP-fold (Vladimir, S. et. Al. Biochemistry 1990, 20, 4509). Furthermore, NPY sequences from a number of animal species have been elucidated and all show a high degree of amino acid homology to the human protein (>94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [Y1, Y2, Y3, Y4(PP), Y5, Y6 (formerly designated as a Y5 receptor)] are recognized today based upon binding profile, pharmacology and/or composition if identity is known (Wahlestedt, C. et. al. Ann. NY Acad. Sci. 1990, 611, 7; Larhammar, D. et. al. J. Biol. Chem. 1992, 267, 10935; Wahlestedt, C. et. al. Regul. Pept. 1986, 13, 307; Fuhlendorff, J. U. et. al. Proc. Natl. Acad. Sci. USA 1990, 87, 182; Grundemar, L. et. al. J. Pharmacol. Exp. Ther. 1991, 258, 633; Laburthe, M. et. al. Endocrinology 1986, 118, 1910; Castan, I. et. al. Endocrinology 1992, 131, 1970; Gerald, C. et. al. Nature 1996, 382, 168; Weinberg, D. H. et. al. Journal of Biological Chemistry 1996, 271, 16435; Gehlert, D. et. al. Current Pharmaceutical Design 1995, 1, 295; Lundberg, J. M. et. al. Trends in Pharmaceutical Sciences 1996, 17, 301). Most and perhaps all NPY receptor proteins belong to the family of so-called G-protein coupled receptors (GPCRs). The neuropeptide Y5 receptor, a putative GPCR, is negatively coupled to cellular cyclic adenosine monophosphate (cAMP) levels via the action of adenylate cyclase (Gerald, C. et. al. Nature 1996, 382, 168; Gerald, C. et. al. PCT WO 96/16542). For example, NPY inhibits forskolin-stimulated cAMP production/levels in a neuroblastoma cell line. A Y5 ligand that mimics NPY in this fashion is an agonist whereas one that competitively reverses the NPY inhibition of forskolin-stimulated cAMP production is an antagonist.

Neuropeptide Y itself is the archetypal substrate for the NPY receptors and its binding can elicit a variety of pharmacological and biological effects in vitro and in vivo. When administered to the brain of live animals (intracerebroventricularly (icv) or into the amygdala), NPY produces anxiolytic effects in established animal models of anxiety such as the elevated plus-maze, Vogel punished drinking and Geller-Seifter's bar-pressing conflict paradigms (Heilig, M. et. al. Psychopharmacology 1989, 98, 524; Heilig, M. et. al. Reg. Peptides 1992, 41, 61; Heilig, M. et. al. Neuropsycho-pharmacology 1993, 8, 357). Thus compounds that mimic NPY are postulated to be useful for the treatment of anxiolytic disorders.

The immunoreactivity of neuropeptide Y is notably decreased in the cerebrospinal fluid of patients with major depression and those of suicide victims (Widdowson, P. S. et. al. Journal of Neurochemistry 1992, 59, 73), and rats treated with tricyclic antidepressants display significant increases of NPY relative to a control group (Heilig, M. et. al. European Journal of Pharmacology 1988, 147, 465). These findings suggest that an inadequate NPY response may play a role in some depressive illnesses, and that compounds that regulate the NPY-ergic system may be useful for the treatment of depression.

Neuropeptide Y improves memory and performance scores in animal models of learning (Flood, J. F. et. al. *Brain Research* 1987, 421, 280) and therefore may serve as a cognition enhancer for the treatment of neurodegenerative diseases such as Alzheimer's Disease (AD) as well as AIDS-related and senile dementia.

Elevated plasma levels of NPY are present in animals and humans experiencing episodes of high sympathetic nerve activity such as surgery, newborn delivery and hemorrhage (Morris, M. J. et. al. *Journal of Autonomic Nervous System* 1986, 17, 143). Thus chemical substances that alter the NPY-ergic system may be useful for alleviating the condition of stress.

Neuropeptide Y also mediates endocrine functions such as the release of luteinizing hormone (LH) in rodents (Kalra, S. P. et. al. *Frontiers in Neuroendrocrinology* 1992, 13, 1). Since LH is vital for mammalian ovulation, a compound that mimics the action of NPY could be useful for the treatment of infertility, particularly in women with so-called luteal phase defects.

Neuropeptide Y is a powerful stimulant of food intake; as little as one-billionth of a gram, when injected directly into the CNS, causes satiated rats to overeat (Clark, J. T. et. al. *Endocrinology* 1984, 115, 427; Levine, A. S. et. al. *Peptides* 1984, 5, 1025; Stanley, B. G. et. al. *Life Sci.* 1984, 35, 2635; Stanley, B. G. et. al. *Proc. Nat. Acad. Sci. USA* 1985, 82, 3940). Thus NPY is orexigenic in rodents but not anxiogenic when given intracerebroventricularly and so antagonism of neuropeptide receptors may be useful for the treatment of eating disorders such as obesity, anorexia nervosa and bulimia nervosa.

In recent years, a variety of potent, structurally distinct small molecule Y1 antagonists has been discovered and developed (Hipskind, P. A. et. al. *Annu. Rep. Med. Chem.* 1996, 31, 1–10; Rudolf, K. et. al. *Eur. J. Pharmacol.* 1994, 271, R11; Serradeil-Le Gal, C. et. al. *FEBS Lett.* 1995, 362, 192; Wright, J. et. al. *Bioorg. Med. Chem. Lett.* 1996, 6, 1809; Poindexter, G. S. et. al. U.S. Pat. No. 5,668,151; Peterson, J. M. et. al. WO9614307 (1996)). However, despite claims of activity in rodent models of feeding, it is unclear if inhibition of a feeding response can be attributed to antagonism of the Y1 receptor.

Several landmark studies strongly suggest that an "atypical Y1" receptor and/or the Y5 receptor, rather than the classic Y1 receptor, is responsible for invoking NPY-stimulated food consumption in animals. It has been shown that the NPY fragment NPY2-36 is a potent inducer of feeding despite poor binding at the classic Y1 receptor (Stanley, B. G. et. al. *Peptides* 1992, 13, 581). Conversely, a potent and selective Y1 agonist has been reported to be ineffective at stimulating feeding in animals (Kirby, D. A. et. al. *J. Med. Chem.* 1995, 38, 4579). More pertinent to the invention described herein, [D-Trp$^{32}$]NPY, a selective Y5 receptor activator has been reported to stimulate food intake when injected into the hypothalamus of rats (Gerald, C. et. al. *Nature* 1996, 382, 168). Since [D-Trp$^{32}$]NPY appears to be a full agonist of the Y5 receptor with no appreciable Y1 activity, the Y5 receptor is hypothesized to be responsible for the feeding response. Accordingly compounds that antagonize the Y5 receptor should be effective in inhibiting food intake, particularly that stimulated by NPY.

N-substituted 2,4-diaminoquinazolines that act as Y5 antagonists are disclosed in (PCT WO 97/20822) and are reported to reduce food consumption in animals. There is no disclosure in this publication, nor in any other that claims Y5 receptor ligands, of an α-substituted β-aminotetralin. The N-substituted aminotetralins described in this application are novel molecular entities that may have binding motifs that are different than other known Y5 ligands and yet bind to a similar region of the Y5 receptor.

SUMMARY OF THE INVENTION

The present invention is relates to compounds of formula I

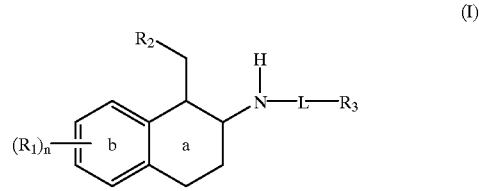

(I)

wherein $R_1$ is independently selected from the group consisting of hydrogen; hydroxy; halo; $C_{1-8}$alkyl; $C_{1-8}$alkoxy; substituted $C_{1-8}$ alkoxy wherein the substituent is selected from halo, such as chloro, bromo, fluoro and iodo; trifluoroalkyl; $C_{1-8}$alkylthio and substituted $C_{1-8}$alkylthio wherein the substituent is selected from halo, such as chloro, bromo, fluoro and iodo, trifluoroalkyl and $C_{1-8}$alkoxy; $C_{3-6}$cycloalkyl; $C_{3-8}$cycloalkyloxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$R_2$ is selected from the group consisting of hydrogen; $C_{1-6}$alkyl; $C_{2-6}$alkenyl; halo, such as fluoro and chloro; $C_{3-7}$cycloalkyl; phenyl; substituted phenyl wherein the substituent is selected from halo, $C_{1-6}$alkyl, $C_{1-6}$alkoxy, trifluoroC$_{1-6}$alkyl, cyano, nitro, amino, $C_{1-6}$alkylamino, and $C_{1-6}$dialkylamino; naphthyl; phenoxy; substituted phenoxy wherein the substituent is selected from halo, $C_{1-6}$alkyl, $C_{1-6}$alkoxy, trifluoroC$_{1-6}$alkyl, cyano and nitro; phenylthio and substituted phenylthio wherein the substituent is selected from halo, $C_{1-6}$alkyl, nitro and amino; a heteroaryl group such pyridyl, pyrimidyl, furyl, thienyl, and imidazolyl; substituted heteroaryl wherein the substituent is selected from $C_{1-6}$alkyl and halo;

L is selected from the group consisting of $C_{1-8}$alkylene; $C_{2-8}$alkenylene; $C_{2-8}$alkynylene; $C_{1-4}$alkyleneC$_{3-8}$cycloalkylene;

$R_3$ is selected from $C_{1-8}$alkyl; substituted $C_{1-8}$alkyl wherein the substituent is selected from alkoxy and halo; alkoxyalkyloxy; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from indolyl, pyridyl, pyrimidyl, furyl, thienyl and imidazolyl; and substituted heteroaryl wherein the substituent is selected from halo, nitro, amino and cyano;

and enantiomers, diastereomers, and pharmaceutically acceptable salts thereof.

As used herein unless otherwise noted the terms "alkyl" and "alkoxy" whether used alone or as part of a substituent group, include straight and branched chains having 1–8 carbon atoms. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. The term "aryl" is intended to include phenyl and naphthyl. The term "halo", unless otherwise indicated, includes bromo, chloro, fluoro and iodo. The term "cycloalkyl" is intended to include cycloalkyl groups having 3–7 carbon atoms. With reference to substituents, the term "independently" means that when more than one of such substituent is possible, such substituents may be the same or different from each other.

Those compounds of the present invention which contain a basic moiety can be converted to the corresponding acid addition salts by techniques known to those skilled in the art. Suitable acids which can be employed for this purpose include hydrochloric, hydrobromic, hydriodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, trifluoracetic acid, p-toluenesulfonic, cyclohexanesulfamic, salicylic, 2-phenoxybenzoic, 2-acetoxybenzoic, and saccharin, and the like. In general, the acid addition salts can be prepared by reacting the free base of compounds of formula I with the acid and isolating the salt.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

The daily dose of the active ingredient to be administered will depend on the age of the patient in need of such treatment, the particular condition to be treated and the manner of administration. Generally, an approximate daily dose of about 10 mg to about 250 mg is to be administered depending upon the mode of administration and the weight of the patient being treated. Determination of optimum doses and frequency of administration for a particular disease state or disorder is within the experimental capabilities of those knowledgeable of the specific disease or disorder being treated.

As modulators of the NPY5 receptor, the compounds of Formula I are useful for treating feeding disorders such as obesity, anorexia nervosa and bulimia nervosa, and abnormal conditions such as epilepsy, depression, anxiety and sexual/reproductive disorders in which modulation of the NPY5 receptor may be useful. The compounds compete with the endogenous ligands NPY and PYY and possibly non-endogenous ligands, and bind to the NPY5 receptor. In addition, the compounds demonstrate antagonist activity by antagonizing the action of NPY upon binding to the Y5 receptor.

The compounds described herein are ligands of the NPY5 receptor, but are not necessarily limited solely in their pharmacological or biological action due to binding to this or any neuropeptide, neurotransmitter or G-protein coupled receptor. For example, the described compounds may also undergo binding to dopamine or serotonin receptors. The compounds described herein are potentially useful in the regulation of metabolic and endocrine functions, particularly those associated with feeding, and as such, may be useful for the treatment of obesity. In addition, the compounds described herein are potentially useful for modulating other endocrine functions, particularly those controlled by the pituitary and hypothalamic glands, and therefore may be useful for the treatment of inovulation/infertility due to insufficient release of luteinizing hormone (LH).

The present invention comprises pharmaceutical compositions containing one or more of the compounds of Formula I. In addition, the present invention comprises intermediates used in their manufacture of compounds of Formula I.

Examples of preferred compounds of formula I include:

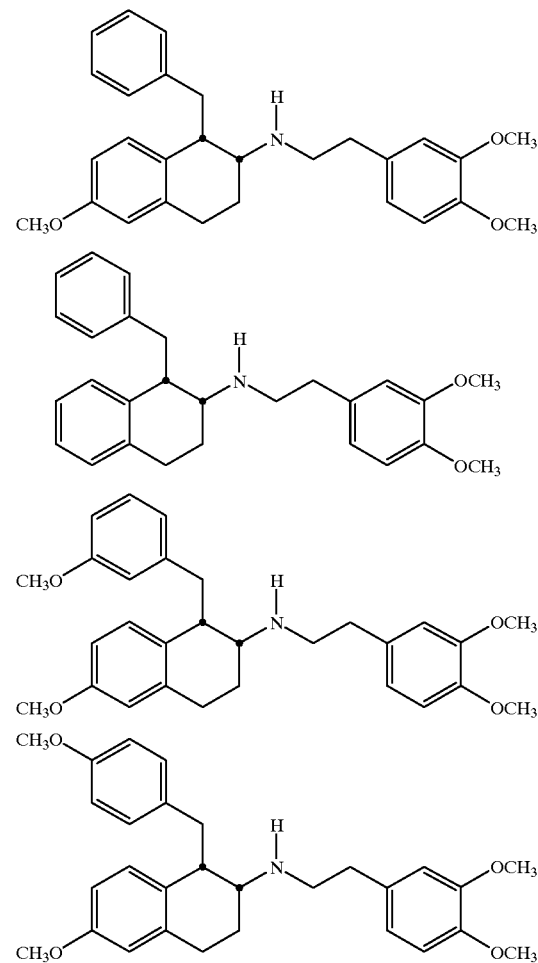

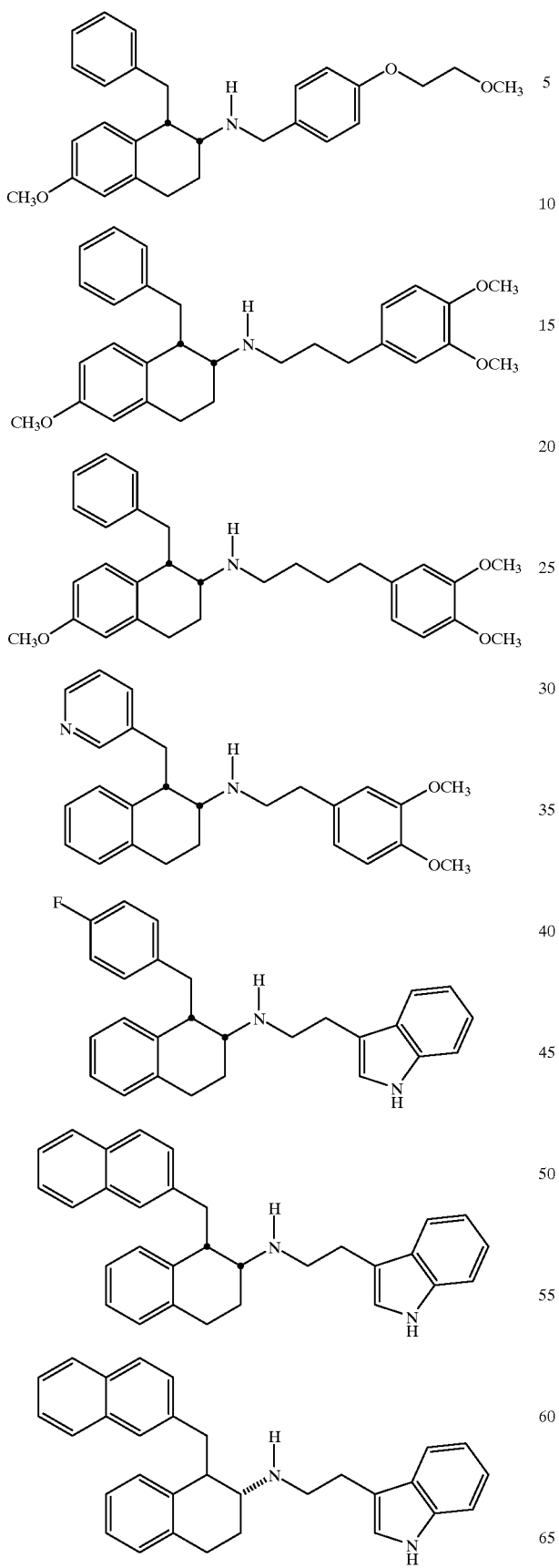
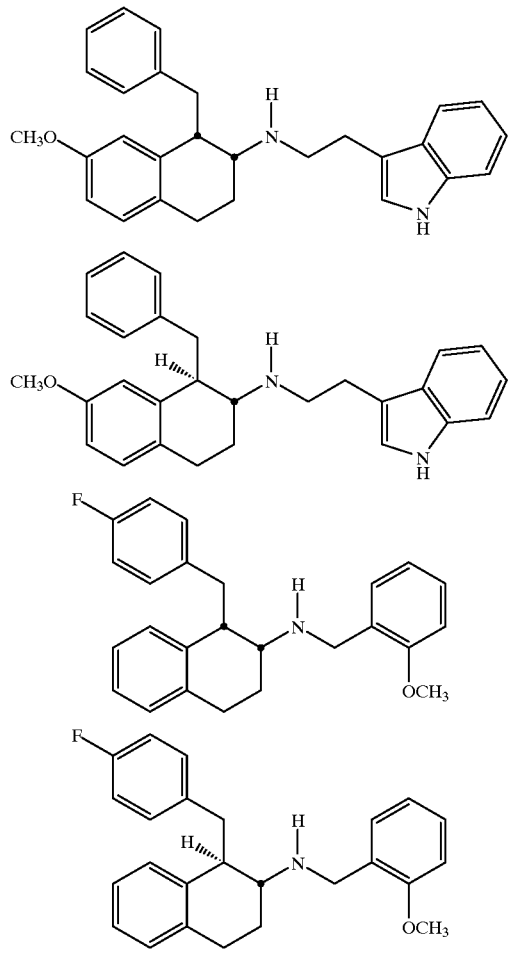

DETAILED DESCRIPTION OF THE INVENTION

The N-substituted aminotetralins of formula I that comprise this invention are synthesized via several distinct chemical syntheses that are described in detail in the Examples below. In general, each synthetic route consists of several sequential chemical operations that can be generalized as described below.

Synthetic Route A:
Introduction of the -substituent onto the tetralone nucleus
Reductive amination of the resultant -substituted--tetralone to afford compounds of formula I
or
Synthetic Route B:
Introduction of the -substituent onto the tetralone nucleus
Conversion to the corresponding α-substituted-β-aminotetralin
Acylation of the aminotetralin
Reduction to regenerate the aminotetralin system to afford compounds of formula I
or
Synthetic Route C:
Introduction of the -substituent onto the tetralone nucleus
Conversion to the corresponding α-substituted-β-aminotetralin
Reductive alkylation of the α-substituted-β-aminotetralin to afford compounds of formula I It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halohydrocarbon solvents. In those cases wherein the product is isolated as the acid addition salt the free base is obtained by techniques known to those skilled in the art.

Specifically, an appropriately substituted -tetralone (II) is reacted with an aryl or heteroaryl aldehyde in the presence of a base such as piperidine, in an inert halohydrocarbon, ethereal or hydrocarbon solvent, such as benzene, at a temperature from ambient temperature to reflux, to afford the corresponding -benzylidenyl--tetralone or -heteroarylmethylidenyl--tetralone (III). The -tetralone (III) is dissolved in an inert hydrocarbon, ethereal, ester or alcohol solvent, such as methanol, and reacted with hydrogen gas from ambient pressure to about 100 p.s.i. in the presence of a suitable catalyst such as, for example, palladium on carbon. The reaction is performed at a temperature from ambient temperature to reflux, to yield the desired -substituted--tetralone product (IV) (Scheme 1).

An alternative method for the preparation of -substituted--tetralones (IV) involves the reaction of an appropriately substituted -tetralone (II) with a base such as pyrrolidine in an inert halohydrocarbon solvent such as dichloromethane or hydrocarbon solvent such as benzene, under Dean-Stark conditions (removal of water) or in an alcohol solvent such as methanol, from ambient temperature to reflux, to afford enamine (V). Alkylation of enamine (V) is accomplished by reaction with a benzylic, heterocyclicalkyl or an allylic halide in an inert solvent such as, for example, acetonitrile, at a temperature from ambient temperature to reflux, to afford the -substituted--iminium salt (VI). Hydrolysis of the salt (VI) to produce the desired -substituted--tetralone product (IV) is accomplished by reaction of (VI) with water and an inorganic or organic acid such as hydrochloric or glacial acetic acid in an inert hydrocarbon, ethereal, alcohol or halohydrocarbon solvent, or a mixture thereof, such as methanol and dichloromethane (Scheme 1).

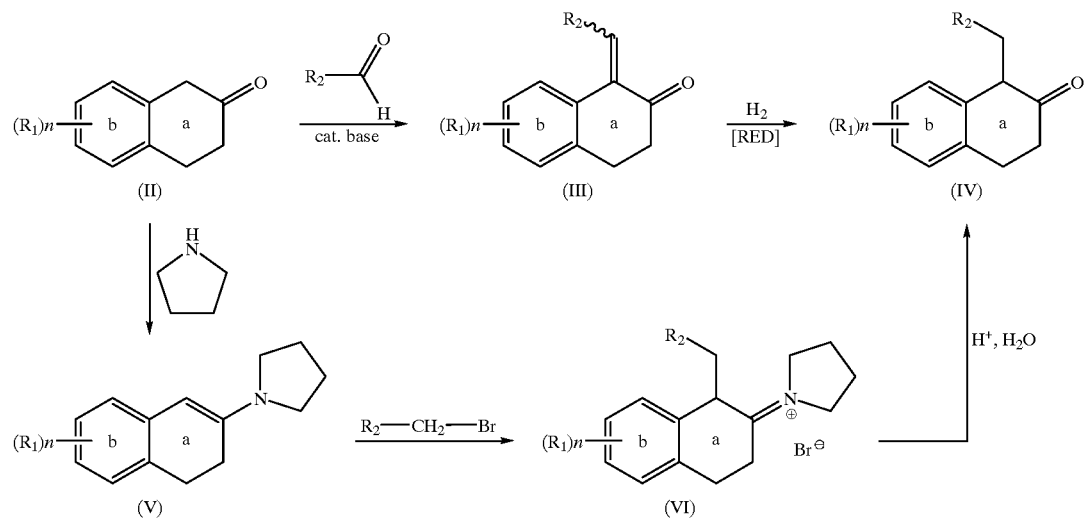

Scheme 1

The N-substituted aminotetralins of formula 1 are prepared by reacting an appropriately -substituted--tetralone (IV) with an amine ($H_2N$-L-$R_3$) in the presence of a reducing agent such as sodium borohydride, or sodium triacetoxyborohydride, for example, in an inert ethereal, halohydrocarbon, or alcohol solvent such as dichloromethane or methanol respectively, at a temperature from ambient temperature to reflux, to yield the desired cis-N-substituted aminotetralin product (I) (Scheme 2). In some cases, the trans-aminotetralin is also formed as a minor product. The cis-aminotetralins (I) can also be isolated as acid addition salts by treatment with an organic or an inorganic acid (HX), such as trifluoroacetic acid or hydrochloric acid, for example (Scheme 2).

Scheme 2

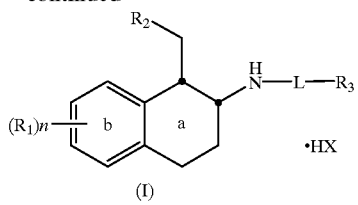

(I)

Alternatively, a -substituted--tetralone (IV) is converted to the corresponding aminotetralin via reaction with an ammonium salt such as ammonium acetate in the presence of a reducing agent such as sodium cyanoborohydride, for example, in an inert halohydrocarbon, hydrocarbon, ethereal or alcohol solvent such as methanol to produce the cis-aminotetralin (VII). In some cases, the trans-aminotetralin (VIII) is also formed as a minor product. The cis-aminotetralins (VII) can also be isolated as acid addition salts by treatment with an organic or an inorganic acid, such as trifluoroacetic acid or hydrochloric acid, for example (Scheme 3).

Scheme 3

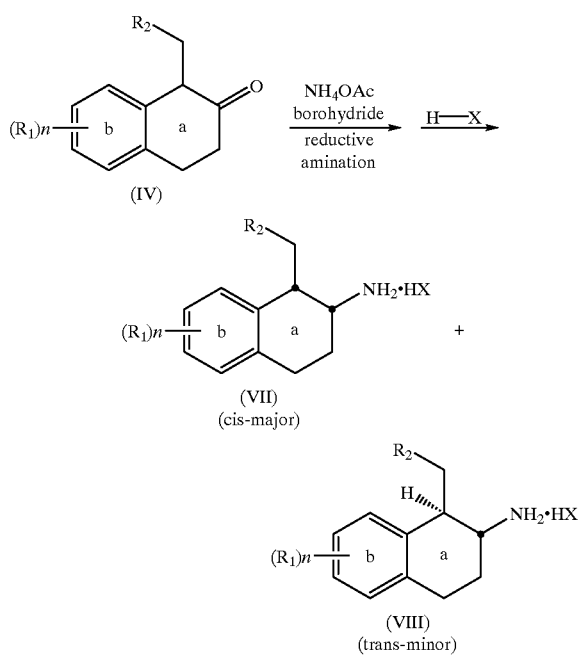

Compound IX is prepared via suitable amidation methods (see Gross and Meienhofer, Eds., "*The Peptides*", Vols. 1–3, Academic Press, New York, N.Y., 1979–1981). A carboxylic acid is converted to an activated ester via peptide coupling methods known to those skilled in the art, and subsequently reacted with an aminotetralin (VII) to afford the corresponding amide product. For example, a carboxylic acid such as 3,4-dimethoxypropionic acid is reacted with HBTU (2-(1H-benzotrazole-1-yl)-1,1,3,3-tetramethyluronium hexafluorophosphate and a β-aminotetralin (VII) in the presence of a base such as diisopropylethylamine, in an inert solvent such as N,N-dimethylformamide, at a temperature from ambient temperature to reflux, to afford amide (IX) respectively.

The N-substituted aminotetralin compounds (I) of the invention are prepared via reduction of tetralinamide (IX) by reaction with a suitable reducing agent such as borane-tetrahydrofuran complex or lithium aluminum hydride in an inert hydrocarbon solvent such as toluene or ethereal solvent such as tetrahydrofuran, at a temperature from ambient temperature to reflux. The final product can be isolated as an acid addition salt upon treatment with a suitable organic acid such as trifluoroacetic acid or inorganic acid such as hydrochloric acid (Scheme 4).

Scheme 4

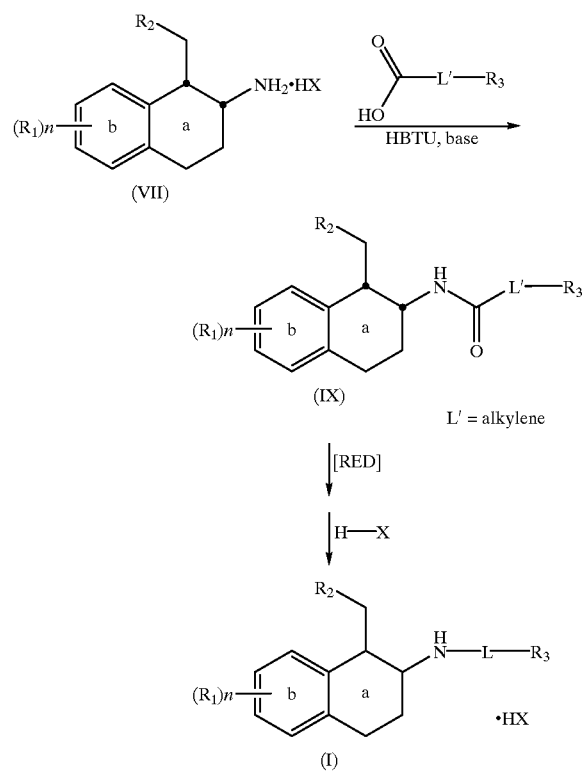

In the above scheme L'=$C_{1-7}$alkykene.

Those compounds of formula (1) wherein L=alkylenecycloalkylene are prepared in the manner described in Scheme 4 above. A cycloalkanecarboxylic acid is reacted with an appropriately substituted β-aminotetralin in the presence of traditional peptide coupling reagents such as DCC, HOBT or HBTU. For example, 2-phenyl-1-cyclopropanecarboxylic acid undergoes coupling to a β-aminotetralin (VII), and upon subsequent reduction, affords an aralkylaminotetralin of formula (1) wherein L=methylenecyclopropylene and $R_3$=phenyl. Compounds of formula (1) wherein L=alkenylene are prepared by coupling a cinnamic acid compound to an appropriately substituted aminotetralin, followed by amide reduction. For example, 3,4-dimethoxycinnamic acid gives an aralkylaminotetralin of formula (1) wherein L=alkenylene and $R_3$=3,4-dimethoxyphenyl. Those compounds wherein L=alkynylene are prepared by reacting an appropriately substituted aminotetralin with a 1-halo-4-aryl-2-alkyne such as, for example, 1-chloro-4-phenylpropyne.

The starting materials used to prepare the novel aralkylaminotetralins of the present invention are either readily available or can be prepared by methods known to those skilled in the art from readily available materials.

EXAMPLES

The following examples describe the invention in greater detail and are intended to illustrate the invention, but not to

13 limit it. All compounds were identified by a variety of methods including nuclear magnetic resonance spectroscopy, mass spectrometry and in some cases, infrared spectroscopy and elemental analysis. Nuclear magnetic resonance (300 MHz NMR) data are reported in parts per million downfield from tetramethylsilane. Mass spectra data are reported in mass/charge (m/z) units. Unless otherwise noted, the materials used in the examples were obtained from readily available commercial sources or synthesized by standard methods known to those skilled in the art. As used hereinafter, hexanes refers either to hexane or a commercially available mixture of hexanes.

Example 1 rac-cis-1-(Phenylmethyl)-6-methoxy-N-(2-(3,4-dimethoxyphenyl)ethyl)-1,2,3,4-tetrahydro-2-naphthalenamine (6)

A. 6-Methoxy--tetralone 1 (3.0 g, 17.0 mmol) was placed in a 250 mL round-bottom flask and dissolved in benzene (90 mL). Pyrrolidine (2.4 mL, 28.8 mmol) was added with stirring and the flask was flushed with argon. A Dean-Stark trap and a reflux condenser were attached and the solution was heated at reflux for 67 hours. After cooling, the solvent was removed in vacuo to yield enamine 2 as an orange glassy solid which was used in subsequent reactions without further purification. MS (MH$^+$) 230; $^1$H NMR (CDCl$_3$) 1.92 (m, 4 H), 2.45 (t, 2H), 2.84 (t, 2H), 3.26 (m, 4H), 3.79 (s, 3H), 5.11 (s, 1H), 6.65 (m, 2H), 6.81 (m, 1H).

B. Enamine 2 was dissolved in acetonitrile (90 mL) in a 250 mL round-bottom flask and benzyl bromide (3.4 mL, 29 mmol) was added to this solution with stirring. The flask was flushed with argon and a reflux condenser was attached. The solution was heated at reflux for 19 hours. After cooling, the solvents were removed in vacuo and the resulting orange glassy solid was triturated with ethyl ether and filtered repeatedly until all traces of the benzyl bromide had been removed. The resulting iminium salt 3 was used in the next step without further purification. MS (MH$^-$) 320.

C. The iminium salt 3 from the previous reaction was transferred to a 500 mL Erlenmeyer flask and methanol (100 mL), dichloromethane (50 mL), water (50 mL), and glacial acetic acid (3 mL) were added. The resulting mixture was flushed with nitrogen, capped, and stirred for 14 hours. The solvents were removed in vacuo. The resulting oil was dissolved in ethyl acetate (250 mL) and washed with water (4×100 mL). The organic extract was dried over magnesium sulfate, filtered, and the solvents removed in vacuo to yield an oily crude product. This material was purified via chromatography (silica gel column (dimensions 2.5×27 cm); 25% ethyl acetate:75% hexanes (v/v) as the eluent). After evaporation of the collected fractions, 3,4-dihydro-6-methoxy-1-(phenylmethyl)-2(1H)-naphthalenone 4 was obtained as a thick yellow oil (2.13 g, 8.0 mmol). MS (MH$^+$) 267; $^1$H NMR (CDCl$_3$) 2.43–2.60 (m, 3H), 2.75–2.81 (m, 1H), 3.18 (dd, 1H), 3.68 (dd, 2H), 3.79 (s, 3H), 6.58–6.91 (m, 5H), 7.15 (m, 3H). (FIG. 1).

FIG. 1

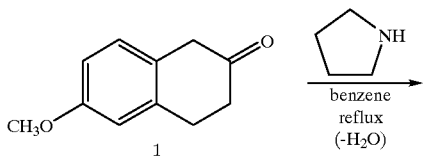

14

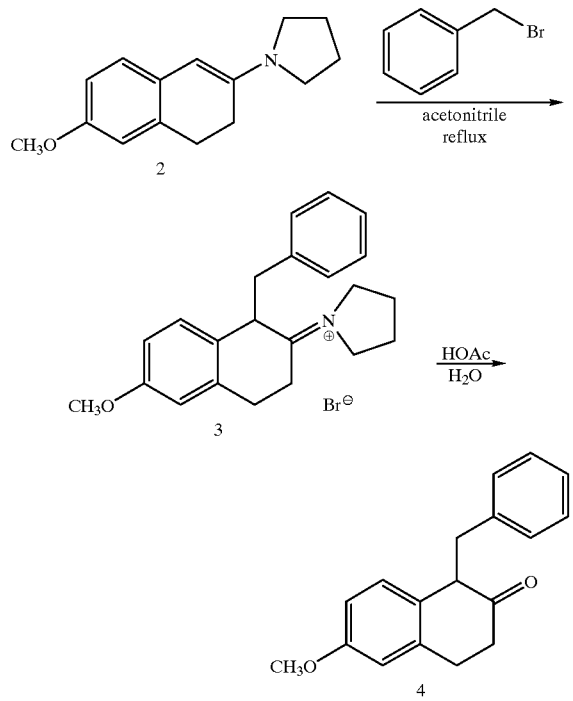

Alternatively, 3,4-dihydro-6-methoxy-1-(phenylmethyl)-2(1H)-naphthalenone 4 is prepared as follows:

B'. 6-Methoxy--tetralone 1 (1.0 g, 5.7 mmol) was dissolved in benzene (25 mL) with stirring in a 50 mL round-bottom flask. Benzaldehyde (0.60 mL, 5.9 mmol) was added to this solution followed by catalytic piperidine (0.014 mL, 0.14 mmol). The flask was flushed with argon and a reflux condenser equipped with a Dean-Stark trap was attached. The solution was heated at reflux for 28 hours and then cooled to room temperature. The solvent was removed in vacuo to yield a dark orange oil. This crude product was dissolved in ethyl ether (100 mL) and then washed with 3N HCl (2×50 mL), water (1×50 mL), and lastly with saturated brine solution (1×50 mL). The organic extract was dried over magnesium sulfate, filtered, and the solvents removed in vacuo. The resultant oil was purified via column chromatography (silica gel column (dimensions 5×25 cm); 25% ethyl acetate:75% hexanes (v/v) as the eluent). After evaporation of the collected fractions, 3,4-dihydro-6-methoxy-1-(phenylmethylidenyl)-2-naphthalenone 5 was obtained as a pale yellow oil (0.70 g, 2.6 mmol) which solidified upon storage in a refrigerator. MS (MH$^+$) 265; $^1$H NMR (CDCl$_3$) 2.54 (t, 2H), 2.98 (t, 2H), 3.79 (s, 3H), 6.63 (dd, 1H), 6.96 (d, 1H), 7.12 (d, 1H), 7.29 (m, 3H), 7.40–7.48 (m, 3H).

C'. Compound 5 (0.464 g, 1.8 mmol) was placed in a 250 mL Parr shaker bottle and dissolved in ethyl acetate (25 mL). Separately, 10% palladium on carbon (0.029 g) was placed in a vial and to it was added methanol (25 mL) in order to create a slurry. This material was then carefully added to the Parr vessel and the mixture was hydrogenated under a pressure of approximately 50 psi for 19 hours. The reaction solution was filtered over a pad of Celite. The solvents were removed in vacuo and the resulting oil was purified by column chromatography (silica gel column (dimensions 2.5×26 cm); 25% ethyl acetate:75% hexanes (v/v) as the eluent). After evaporation of the collected fractions, 3,4-dihydro-6-methoxy-1-(phenylmethyl)-2(1H)-naphthalenone 4 was obtained as an off-white oil (0.40 g, 1.50 mmol) (FIG. 2).

FIG. 2

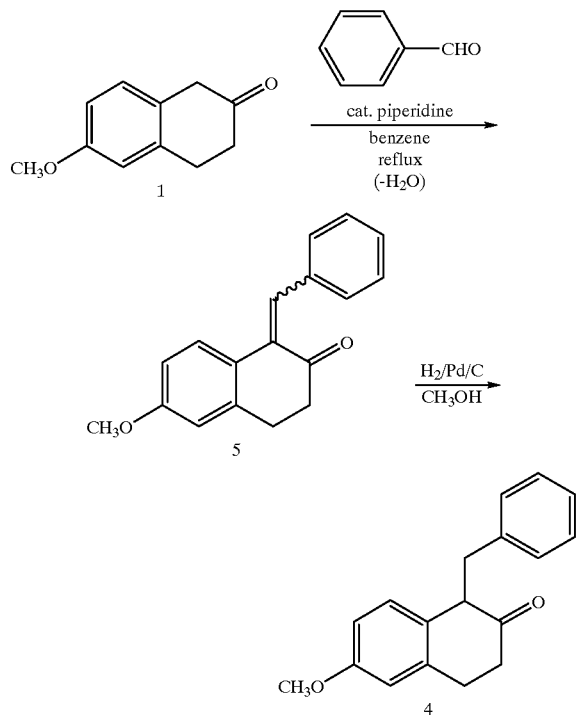

D. 1-Benzyl-6-methoxy-1,2,3,4-tetrahydronaphthalen-2-one 4 (0.134 g, 0.503 mmol) was dissolved in dichloromethane (5 mL) in a round-bottom flask. 3,4-Dimethoxyphenethylamine (0.085 mL, 0.504 mmol) and glacial acetic acid (0.029 mL, 0.507 mmol) were added to the stirred tetralone solution. Sodium triacetoxyborohydride (0.150 g, 0.708 mmol) was added to the resulting solution, the flask was flushed with nitrogen and the solution was allowed to stir for 16 hours. After this time, the reaction solution was extracted with 1 M sodium hydroxide solution (1×15 mL). The aqueous phase was back extracted with ethyl ether (3×15 mL). The combined organic extracts were dried over magnesium sulfate, filtered, and the solvents were removed in vacuo. Ethyl ether was added to dissolve the resulting oily product. An excess of 1 M hydrogen chloride in ethyl ether was added to the ether solution which resulted in the precipitation of the crude product as the HCl salt. The crude salt was triturated with ethyl ether to yield a tan powder. The crude product was purified via chromatography (silica gel column (dimensions 2.5×16 cm) 98% dichloromethane/1% methanol/1% concentrated ammonium hydroxide solution as eluent)). After evaporation of the collected fractions, the product was dissolved in ethyl ether and an excess of hydrogen chloride in ether was added which caused a solid to precipitate. The solid was triturated with ethyl ether, filtered and dried via aspiration to afford rac-cis-1-(phenylmethyl)-6-methoxy-N-(2-(3,4-dimethoxyphenyl)ethyl)-1,2,3,4-tetrahydro-2-naphthalenamine 6 HCl salt as a tan powder (0.051 g, 0.11 mmol) (92% pure by HPLC) (FIG. 3) MS: M+1=432 NMR($d_6$-DMSO): 9.43 (br, 1H), 9.27 (br, 1H), 7.32–7.15 (m, 3H), 7.11 (d, 2H), 6.94 (m, 2H), 6.82 (m, 1H), 6.68 (d, 1H), 6.33 (dd, 1H), 5.88 (d, 1H), 3.79 (s, 3H), 3.74 (s, 3H), 3.66 (s, 3H), 3.60–3.48 (m, 1H), 3.47–3.14 (m, 4H), 3.13–2.98 (m, 3H), 2.97–2.80 (m, 1H), 2.44 (t, 1H), 2.32–2.20 (m, 1H), 2.19–2.02 (m, 1H).

FIG. 3

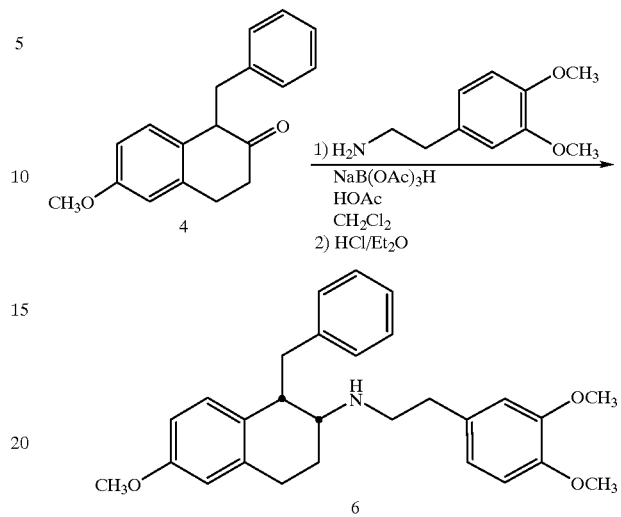

Example 2 rac-cis-1-(Phenylmethyl)-6-methoxy-N-(2-(3-indolyl)ethyl)-1,2,3,4-tetrahydro-2-naphthalenamine hemifumarate (8)

A. The enamine of -tetralone was prepared as described in Example 1 (also see Stork, G.; Brizzolara, A.; Landesman, H.; Szmuskovicz, J.; Terrell, R. *J. Am. Chem. Soc.* 1963, 85, 207). A solution of -tetralone (25.0 g, 170 mmol) and pyrrolidine (19.9 g, 280 mmol) in benzene (500 mL) was heated in a round bottom flask fitted with a condenser and Dean-Stark trap. After 20 h of heating at reflux, the reaction mixture was cooled and concentrated to provide 35.0 g (quantitative yield) of the desired enamine as a beige solid. This material was used without purification.

B. The enamine described above was alkylated with benzyl bromide as described In Example 1 (also see Jensen, B. L.; Michaud, D. P. *Synthesis* 1977, 848). Benzyl bromide (45.7 g, 267 mmol) was added to a solution of the enamine (33.3 g, 167 mmol) in acetontrile (400 mL) which had been dried over 4A molecular sieves. This mixture was heated at reflux under nitrogen for 20 h. After cooling, the reaction mixture was concentrated in vacuo to provide an orange-brown semisolid. Trituration with acetone followed by filtration gave the corresponding iminium salt as an orange-beige solid.

C. Chloroform (50 mL), glacial acetic acid (100 mL), and water (400 mL) were added to the iminium salt, and the resulting mixture was stirred at ambient temperature for 20 h. Additional chloroform was added to the reaction mixture, and the layers were separated. The organic layer was washed with water, dried ($Na_2SO_4$), and concentrated to give 41.7 g of a dark brown oil. Approximately half of this material was purified on a Waters Delta Prep 300 LC apparatus using a gradient of 0–100% chloroform in hexanes over 200 min. to give 14.93 g of desired product as an orange oil. The impure product-containing fractions were combined and concentrated and combined with the second half of the originally isolated crude product and purified on a Waters Delta Prep 300 LC apparatus using a gradient of 20–100% chloroform in hexanes over 200 min. to give an additional 18.96 g of desired product. The total yield of 3,4-dihydro-1-(phenylmethyl)-2(1H)-naphthalenone 7 was 33.89 g (84%).

MS (CI-CH$_4$), m/z 237 (MH$^+$). $^1$H NMR (CDCl$_3$) 2.37–2.64 (m, 3H), 2.75–2.87 (m, 1H), 3.12–3.30 (m, 2H), 3.72 (t, J=6.3 Hz, 1 H), 6.81–6.95 (m, 3H), 7.08–7.22 (m, 6H).

D. Sodium cyanoborohydride (1.59 g, 25.3 mmol) was added to a solution of naphthalenone 7 (3.00 g, 12.7 mmol), tryptamine (2.03 g, 12.7 mmol), and acetic acid (0.76 g, 12.7 mmol) in methanol (100 mL). The reaction mixture was stirred for 20 h under nitrogen and then concentrated in vacuo to provide an orange-yellow solid. Saturated aqueous sodium carbonate solution was added to this residue, and the resulting mixture was extracted with chloroform. The chloroform extracts were combined, dried (Na$_2$SO$_4$), and concentrated to provide an orange-brown foam which was purified on flash silica gel (10% hexanes-chloroform to 1% methanol-chloroform) to provide the desired product as a red-beige foam. This material was dissolved in a minimum amount of acetone, and fumaric acid (0.84 g) was added. Diethyl ether and hexanes were added to precipitate a cream-colored solid and this material was crystallized from methanol to give 1.75 g (31%) of rac-cis-1-(phenylmethyl)-6-methoxy-N-(2-(3-indolyl)ethyl)-1,2,3,4-tetrahydro-2-naphthalenamine hemifumarate 8 (FIG. 4). mp 241.5–244.5° C. MS (PB-CH$_4$), m/z 381 (MH$^+$). $^1$H NMR (DMSO-d$_6$) 1.80–2.00 (m, 2H), 2.40–2.50 (m 1H), 2.78–2.90 (m, 1H), 2.88–3.24 (m, 9H), 6.27 (d, J=7.7 Hz, 1H), 6.54 (s, 1H), 6.80 (br t, J=7.1 Hz, 1H), 6.88–7.28 (m, 11H), 7.35 (d, J=6.9 Hz, 1H), 7.57 (d, J=7.7 Hz, 1 H), 10.88 (br s, 1H).

Elemental analysis: Calculated for C$_{27}$H$_{28}$N$_2$·0.5 C$_4$H$_4$O$_4$: C, 79.42; H, 6.89; N, 6.39. Found C, 79.62; H, 6.93; N, 6.39.

Sodium cyanoborohydride (1.53 g, 24.4 mmol) was added to a solution of 1-benzyl--tetralone (2.88 g, 12.2 mmol), prepared as described in Example 2, 4-fluorobenzylamine (1.53 g, 12.2 mmol), and acetic acid (0.73 g, 12.2 mmol) in methanol (100 mL) under nitrogen. After 20 h of stirring, the reaction mixture was concentrated in vacuo to provide a yellow solid. Saturated aqueous sodium carbonate solution (100 mL) was added to this residue, and the resulting mixture was extracted with chloroform. The chloroform extracts were combined, dried (Na$_2$SO$_4$), and concentrated to provide a yellow-brown oil which was purified on flash silica gel (25% hexanes-chloroform ) to provide 3.80 g of a dark brown oil. This material was purified on flash silica gel (25% hexanes-chloroform) to provide 2.39 g of a red-brown oil. This material was dissolved in methanol (40 mL), and 48% hydrobromic acid (0.73 mL) was added. Upon addition of diethyl ether (900 mL), a solid precipitated out of solution. Crystallization from acetonitrile with decolorizing charcoal and diethyl ether gave 0.58 g of light grey needles. A second recrystallization was done to provide 0.27 g (5%) of rac-cis-1-(phenylmethyl)-N-(4-fluorophenylmethyl)-1,2,3,4-tetrahydro-2-naphthalenamine monohydrobromide 9 as a fluffy white powder (FIG. 5). mp 251.5–252.5° C. MS (PB-CH$_4$), m/z 346 (MH$^+$). $^1$H NMR (DMSO-d$_6$) 2.08–2.23 (m, 1H), 2.26–2.35 (br s, 1H), 2.83–3.00 (m, 1H), 3.07–3.20 (m, 2H), 3.25–3.45 (br m, 2H), 3.55–3.68 (br d, 1H), 4.40 (AB quartet, 2H), 5.98 (d, J=7.4 Hz, 1H), 6.74 (t, 1H), 6.97–7.15 (m, 4H), 7.16–7.29 (m, 3H), 7.35 (t, J=8.8 Hz, 1H), 7.67 (dd, J=8.7, 5.6 Hz, 2 H).

Elemental analysis: Calculated for C$_{24}$H$_{24}$FN·HBr: C, 67.61; H, 5.91; N, 3.29; Br, 18.74; F, 4.46. Found C, 67.47; H, 5.89; N, 3.12; Br, 17.97; F, 4.26.

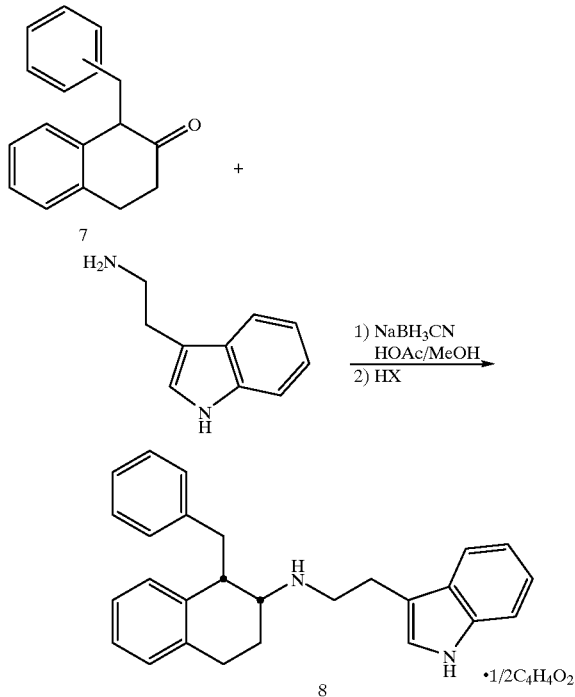

Example 3 rac-cis-1-(Phenylmethyl)-N-(4-fluorophenylmethyl)-1,2,3,4-tetrahydro-2-naphthalenamine monohydrobromide (9)

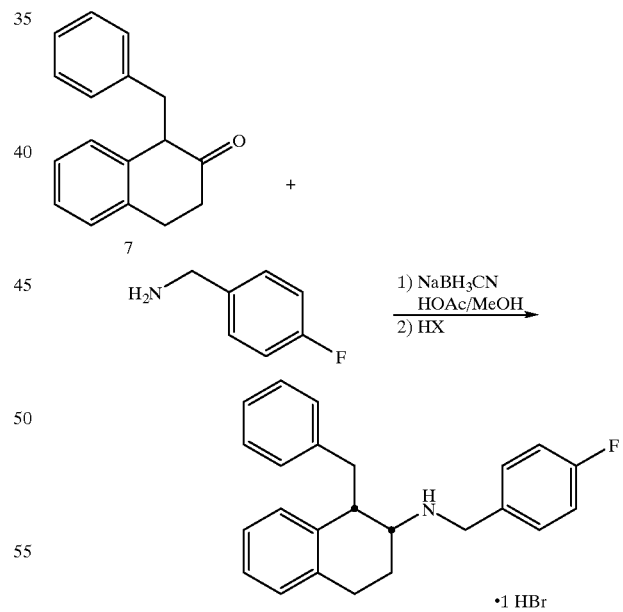

Example 4 rac-cis-1-(Phenylmethyl)-N-(2-methoxyphenylmethyl)-1,2,3,4-tetrahydro-2-naphthalenamine (11); and rac-cis-1-(Phenylmethyl)-N-(2-methoxyphenylmethyl)-1,2,3,4-tetrahydro-2-naphthalenamine monohydrobromide (11a)

A. 1-Benzyl-1,2,3,4-tetrahydro-2-naphthalenamine was prepared following literature procedures (Danheiser, R. L.;

Morin, J. M., Jr.; Salaski, E. J. *J. Am. Chem. Soc.* 1985, 107, 8066; Ghosh, A.; Wang, W.; Freeman, J. P.; Althaus, J. S.; VonVoigtlander, P. F.; Scahill, T. A.; Mizsak, S. A.; Szmuskovicz, J. *Tetrahedron* 1991, 47, 8653). Sodium cyanoborohydride (0.24 g, 3.81 mmol) was added to a suspension of 1-benzyl--tetralone (0.90 g, 3.81 mmol), ammonium acetate (2.94 g, 3.81 mmol), and powdered unactivated 3A molecular sieves in 2-propanol (21 mL) under nitrogen. After 50 h of stirring, the reaction mixture was filtered through Dicalite. The filter cake was washed with methanol and chloroform. The combined filtrates were concentrated in vacuo to provide a cream-colored solid. Saturated aqueous potassium carbonate solution was added to this material until basic, and the resulting mixture was extracted with chloroform. The chloroform extracts were combined, dried ($Na_2SO_4$), and concentrated to provide a colored oil which was purified on flash silica gel (2.5% methanol-chloroform to 5% methanol-chloroform) to provide 0.38 g of 2-amino-1-benzyltetralin 10 as a brown oil (FIG. 6). $^1$H NMR ($CDCl_3$) 1.30 (br s, exchangeable, 2H), 1.74–1.93 (m 2H), 2.75–3.13 (m, 5H), 3.16–3.27 (m 1H), 6.74 (d, J=7.6 Hz, 1 H), 6.89–7.00 (m, 1H), 7.01–7.30 (m, 7H).

B. 2-Anisaldehyde (0.22 g, 1.60 mmol) was added to a solution of 2-amino-1-benzyltetralin 10 (0.38 g, 1.60 mmol) and acetic acid (0.096 g, 1.60 mmol) in 1,2-dichloroethane (20 mL) and sodium triacetoxyborohydride (0.51 g, 2.40 mmol) under nitrogen. The resulting suspension was stirred for 5 days and then concentrated in vacuo to provide a yellow film. Saturated aqueous potassium carbonate solution (40 mL) and chloroform (40 mL) were added to this material. The layers were separated, and the aqueous layer was extracted with chloroform. The chloroform extracts were combined, dried ($Na_2SO_4$), and concentrated to provide 0.51 g of rac-cis-1-(phenylmethyl)-N-(2-methoxyphenylmethyl)-1,2,3,4-tetrahydro-2-naphthalenamine 11 as a brown oil.

FIG. 6

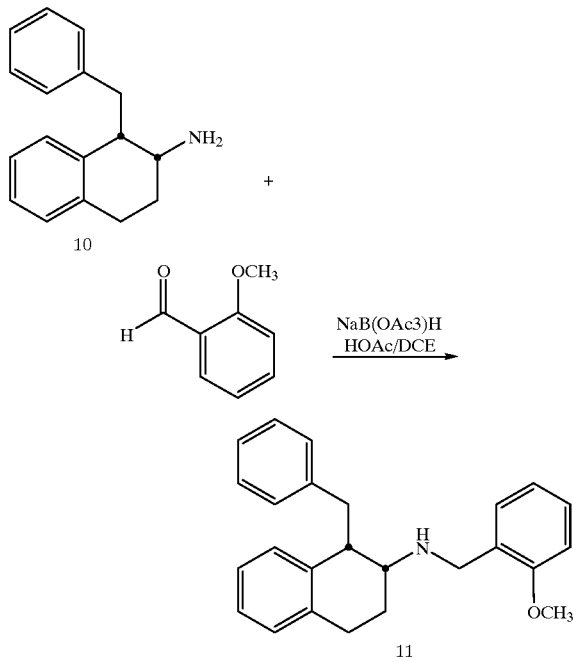

Alternatively, compound 11 was prepared as follows:

A. Sodium cyanoborohydride (0.46 g, 7.28 mmol) was added to a solution of 1-benzyl-2-tetralone (0.86 g, 3.64 mmol), 2-methoxybenzylamine (0.50 g, 3.64 mmol), and acetic acid (0.22 g, 3.64 mmol) in methanol (10 mL) under nitrogen. After 48 h of stirring, the reaction mixture was concentrated in vacuo to provide a brown oil. Saturated aqueous sodium carbonate solution (25 mL) was added to this residue and the resulting mixture was extracted with chloroform. The chloroform extracts were combined, dried ($Na_2SO_4$), and concentrated to provide a brown oil which was purified on flash silica gel (1% methanol-chloroform to 5% methanol-chloroform) to provide 1.0 g of 1-benzyl-2-(2-methoxybenzylamino)tetralin as a brown oil.

This reaction sequence was repeated on a larger scale. Sodium cyanoborohydride (1.71 g, 27.3 mmol) was added to a solution of 1-benzyl--tetralone (3.22 g, 13.6 mmol), 2-methoxybenzylamine (1.87 g, 13.6 mmol), and acetic acid (0.82 g, 13.6 mmol) in methanol (40 mL) under nitrogen. After 20 h of stirring, TLC (thin layer chromatography) analysis indicated that reaction was ca. 75% complete so an additional 0.85 g of sodium cyanoborohydride was added to the reaction mixture. After 16 h of additional stirring, the reaction mixture was concentrated in vacuo to provide a yellow solid. Saturated aqueous sodium carbonate solution (25 mL) was added to this residue and the resulting mixture was extracted with chloroform. The chloroform extracts were combined, dried ($Na_2SO_4$), and concentrated to provide 4.07 g of an orange-brown oil. This material was combined with the crude batches of cis-1-benzyl-2-(2-methoxybenzylamino)tetralin whose preparation was described above and purified on flash silica gel (1% methanol-chloroform to 2.5% methanol-chloroform) to provide 1.82 g of pure desired product as a brown oil in addition to 0.85 g of product with a trace amount of an impurity by TLC as well as 1.01 g of impure product as an orange-brown oil. The pure product was dissolved in methanol (75 mL), and hydrobromic acid (0.57 mL) was added. When diethyl ether (900 mL) was added, a cream-colored solid precipitated out of solution. The nearly pure product was dissolved in methanol, and 48% hydrobromic acid (0.27 mL) was added. Diethyl ether (900 mL) was added and a cream-colored solid precipitated out of solution. The impure material (1.01 g) was purified on flash silica gel (10% hexanes-chloroform to pure chloroform) to provide an additional 0.46 g of desired product as a golden-brown oil. This material was dissolved in methanol (5 mL), and hydrobromic acid (0.14 mL) was added. When diethyl ether (500 mL) was added, a cream-colored solid precipitated out of solution. These solids were independently collected; TLC analysis indicated they were identical and so the crude salts were combined and crystallized from methanol with decolorizing charcoal to give 2.24 g (24%) of rac-cis-1-(phenylmethyl)-N-(2-methoxyphenylmethyl)-1,2,3,4-tetrahydro-2-naphthalenamine monohydrobromide 11a as white fluffy needles, mp 246.5–250.5° C. MS ($CI-CH_4$), m/z 358 ($MH^+$). $^1$H NMR (DMSO-$d_6$) 2.03–2.18 (m, 1H), 2.16–2.29 (br m, 1H), 2.83–3.18 (m, 5H), 3.23–3.40 (m, 2H), 3.58–3.69 (br m, 1H), 3.83 (s, 3H), 5.99 (d, J=7.6 Hz, 1H), 6.75 (brt, J=6.7 Hz, 1H), 6.96 (t, J=7.4 Hz, 1H), 6.99–7.16 (m, 4H), 7.17–7.32 (m, 4H), 8.74–8.92 (br s, 1H), 8.90–9.12 (br, s, 1H).

Elemental analysis: Calculated for $C_{25}H_{27}NO \cdot HBr$: C, 68.49; H, 6.44; N, 3.19; Br, 18.23. Found C, 68.51; H, 6.41; N, 3.14; Br, 18.62.

Example 5 rac-cis-1-(4-Fluorophenylmethyl)-N-(2-methoxyphenylmethyl)-1,2,3,4-tetrahydro-2-naphthalenamine monohydrobromide (12)

A. The preparation of 1-(4-fluorobenzyl)--tetralone was carried out in a manner similar to that described in Example 2 for 1-benzyl--tetralone. A solution of -tetralone (10.0 g, 68.4 mmol) and pyrrolidine (8.0 g, 112 mmol) in benzene (200 mL) was heated in a round bottom flask fitted with a condenser and Dean-Stark trap. After 2 days of reflux, the reaction mixture was cooled and concentrated to provide the desired enamine as a brown-grey foam. This material was used without purification.

B. 4-Fluorobenzyl bromide (20.7 g, 109 mmol) was added to a solution of the enamine in acetonitrile (200 mL) which had been dried over 4A molecular sieves. This mixture was heated at reflux under nitrogen for 3 days. After cooling, the reaction mixture was concentrated in vacuo to provide a brown solid. Chloroform (25 mL), glacial acetic acid (50 mL), and water (200 mL) were added to this material and the resulting mixture was stirred at ambient temperature for 20 h. Additional chloroform was added to the reaction mixture, and the layers were separated. The organic layer was washed with water, dried ($Na_2SO_4$), and concentrated to give 24.2 g of the corresponding -benzyl--tetralone as a dark brown oil. This material was purified on a flash silica gel column (25% hexanes-chloroform) to provide 17.9 g of a red oil which was purified further on a flash silica gel column (1:1 hexanes-chloroform) to provide 12.1 g (70%) of desired product, 1-(4-fluorobenzyl)--tetralone, as a yellow oil. MS (CI-$CH_4$), m/z 255 (MH$^+$). $^1$H NMR ($CDCl_3$) 2.38–2.56 (m, 3H), 2.76–2.86 (m 1H), 3.21 (AB octet, J=15.5, 6.8 Hz, 2H), 3.70 (t, J=6.2 Hz, 1 H), 6.75–6.85 (m, 4H), 6.93 (dd, J=7.5, 2.8 Hz, 1H), 7.09–7.22 (m, 3H).

C. Sodium cyanoborohydride (2.05 g, 32.6 mmol) was added to a solution of 1-(4-fluorobenzyl)-β-tetralone (4.15 g, 16.3 mmol), 2-methoxybenzyl amine (1.79 g, 13.1 mmol), and acetic acid (0.78 g, 13.1 mmol) in methanol (150 mL). The reaction mixture was stirred for 20 h under nitrogen and then concentrated in vacuo to provide a brown foam. Saturated aqueous sodium carbonate solution (100 mL) was added to this residue and the resulting mixture was extracted with chloroform. The chloroform extracts were combined, dried ($Na_2SO_4$), and concentrated to provide 5.92 g of a red-brown foam which was purified on flash silica gel (1:1 hexanes-chloroform to 30:70 hexanes-chloroform) to provide pure cis isomer as 1.92 g of a brown oil. This material was dissolved in methanol (25 mL), and 48% hydrobromic acid (0.53 mL) was added. Diethyl ether (900 mL) was added and a cream-colored solid precipitated out of solution. In addition to 1.92 g of pure cis isomer, 1.69 g of slightly less pure cis material were isolated. This material was dissolved in methanol (25 mL), and 48% hydrobromic acid (0.46 mL) was added. Diethyl ether (900 mL) was added which produced a pale-pink precipitate. These solids were independently collected, and were identical by TLC. These materials were combined and crystallized from methanol with decolorizing charcoal to give 2.24 g (28%) of rac-cis-1-(4-fluorophenylmethyl)-N-(2-methoxyphenylmethyl)-1,2,3,4-tetrahydro-2-naphthalenamine monohydrobromide 12 as white feathery crystals. mp 253.5–255° C. MS (CI-$CH_4$), m/z 376 (MH$^+$). $^1$H NMR (DMSO-$d_6$) 2.05–2.30 (m, 2H), 2.84–3.02 (m, 1H), 3.04–3.23 (m, 2H), 3.42 (br d, J=11.8 Hz, 2H), 3.53–3.68 (br m, 1H), 3.84 (s, 3H), 4.39 (b AB quartet, 2H), 5.98 (d, J=7.7 Hz, 1H), 6.78 (t, J=7.7 Hz, 1H), 6.99–7.16 (m, 8H), 7.47 (t, J=7.9 Hz, 1H), 7.54 (d, J=7.4 Hz, 1 H), 8.68–8.88 (br s, 1H), 9.00–9.22 (br s, 1H).

Elemental analysis: Calculated for $C_{25}H_{26}FNO \cdot HBr$: C, 63.94; H, 6.37; N, 2.90; Br, 16.55; F, 3.93. Found C, 63.81; H, 5.74; N, 2.91; Br, 16.19; F, 4.19.

Example 6 rac-trans-1-(4-Fluorophenylmethyl)-N-(2-methoxyphenylmethyl)-1,2,3,4-tetrahydro-2-naphthalenamine monooxalate (13)

From the chromatography described above in Example 5, 0.29 g of pure rac-trans-1-(4-fluorophenylmethyl)-N-(2-methoxyphenylmethyl)-1,2,3,4-tetrahydro-2-naphthalenamine was isolated as a golden brown oil. In addition, a mixture of the cis and trans naphthalenamines was isolated as 0.60 g of a brown oil. This material was purified via flash silica gel column chromatography (1:1 hexanes-chloroform to 1:3 hexanes-chloroform) to provide pure trans isomer as 0.53 g of a yellow glass. The two pure batches of trans isomer were combined, dissolved in methanol (5 mL), and oxalic acid (0.16 g) was added. Upon addition of diethyl ether (150 mL) and hexanes (600 mL), a white solid precipitated out of solution. Crystallization from acetonitrile with decolorizing charcoal and diethyl ether gave 0.20 g (3%) of rac-trans-1-(4-fluorophenylmethyl)-N-(2-methoxyphenylmethyl)-1,2,3,4-tetrahydro-2-naphthalenamine monooxalate 13 as a snow-white powder. mp 191.5–193.5° C. MS (CI-$CH_4$), m/z 376 (MH$^+$). $^1$H NMR (DMSO-$d_6$) 1.92–2.09 (br m, 1H), 2.14–2.30 (br m, 1H), 2.67–3.00 (m, 6H), 3.13–3.26 (br m, 1H), 3.30–3.42 (br m,1H), 3.71 (s, 3H), 6.90 (t, J=7.3 Hz, 1H), 6.99 (d, J=8.2 Hz, 1H), 7.08–7.32 (m, 10H), 7.36 (t, 1H).

Elemental analysis: Calculated for $C_{25}H_{26}FNO \cdot C_2H_2O_4$: C, 69.66; H, 6.06; N, 3.01; F, 4.08. Found C, 69.33; H, 6.03; N, 3.08; F, 4.28.

Example 7 rac-cis-1-(Phenylmethyl)-N-(4-fluorophenylmethyl)-1,2,3,4-tetrahydro-2-naphthalenamine monohydrobromide (14)

Sodium cyanoborohydride (1.49 g, 23.4 mmol) was added to a solution of 1-benzyl--tetralone (2.80 g, 11.8 mmol), prepared as described in Example 2, and 4-fluorophenethylamine hydrochloride (2.08 g, 11.8 mmol) in methanol (150 mL) under nitrogen. After 20 h of stirring, the reaction mixture was concentrated in vacuo to provide a yellow-brown solid. Saturated aqueous sodium carbonate solution (100 mL) was added to this residue and the resulting mixture was extracted with chloroform. The chloroform extracts were combined, dried ($Na_2SO_4$), and concentrated to provide 4.46 g of a yellow-brown oil which was purified on flash silica gel (1:1 hexanes-chloroform) to provide 3.70 g of a red-brown oil. This material was purified on a flash silica gel column (1:1 hexanes-chloroform) to provide 3.10 g of red-brown oil. A third purification was performed on another flash silica gel column (1:1 hexanes-chloroform) to provide 2.36 g of a brown oil. This material was dissolved in methanol (20 mL), and 48% hydrobromic acid (0.66 mL) was added. Upon addition of diethyl ether (950 mL), a white solid precipitated out of solution. Crystallization from methanol gave 1.32 g (25%) of rac-cis-1-(phenylmethyl)-N-(4-fluorophenylmethyl)-1,2,3,4-tetrahydro-2-naphthalenamine monohydrobromide 14 as a fluffy snow-white powder. mp 259–260.5° C. MS (CI-$NH_3$), m/z 360 (MH$^+$). $^1$H NMR (DMSO-$d_6$) 2.02–2.12 (br m, 1H), 2.11–2.32 (br m, 1H), 2.82–3.00 (br m, 1H), 3.00–3.21 (br m, 4H), 3.20–3.52 (m, 5H), 3.52–3.70 (br m, 1H), 5.99 (d, J=7.6 Hz, 1H), 6.74 (t, J=6.7 Hz, 1H), 6.98–7.19 (m, 4H), 7.18–7.32 (m, 5H), 7.32–7.45 (m, 2H), 8.75–9.10 (m, 2H).

Elemental analysis: Calculated for $C_{25}H_{26}FN \cdot HBr$: C, 68.18; H, 6.18; N, 3.18; Br, 18.14; F, 4.31. Found C, 67.96; H, 6.04; N, 3.00; Br, 18.12; F, 4.51.

Example 8 rac-cis-1-(Phenylmethyl)-7-methoxy-N-(2-methoxyphenylmethyl)-1,2,3,4-tetrahydro-2-naphthalenamine monohydrobromide (15)

A. A solution of 7-methoxy--tetralone (5.0 g, 28.4 mmol) and pyrrolidine (3.31 g, 46.5 mmol) in benzene (80 mL) was heated in a round bottom flask fitted with a condenser and Dean-Stark trap. After 20 h of heating at reflux, the reaction mixture was cooled and concentrated to provide the enamine as a brown oil. This material was used without purification.

B. Benzyl bromide (7.76 g, 109 mmol) was added to a solution of the enamine in acetonitrile (100 mL) which had been dried over 4A molecular sieves. This mixture was heated at reflux under nitrogen for 20 h. After cooling, the reaction mixture was concentrated in vacuo to provide an orange foam. Chloroform (12.5 mL), glacial acetic acid (25 mL) and water (100 mL), were added to this material and the resulting mixture was stirred at ambient temperature for 20 h. Additional chloroform was added to the reaction mixture, and the layers were separated. The organic layer was washed with water, dried ($Na_2SO_4$), and concentrated to give 10.31 g of a red-brown oil. This material was purified on flash silica gel (1:1 hexanes-chloroform to 1:3 hexanes-chloroform) to provide 2.60 g of pure product as an orange oil in addition to 1.99 g of a brown oil which was purified on flash silica gel (1:1 hexanes-chloroform to 1:3 hexanes-chloroform) to provide an additional 1.62 g of desired product as a brown oil. The total yield of 1-benzyl-7-methoxy--tetralone was 4.22 g (56%). $^1$H NMR ($CDCl_3$) 2.36–2.61 (m, 3H), 2.74–2.82 (m 1H), 3.18 (AB octet, J=13.3, 7.4 Hz, 2H), 3.60–3.70 (m, 4H), 6.39 (d, J=2.5 Hz, 1H), 6.72 (dd, J=8.3, 2.7 Hz, 1H), 6.86–6.94 (m, 2H), 7.04 (d, J=8.3 Hz, 1H), 7.14–7.20 (m, 3H).

C. Sodium cyanoborohydride (0.84 g, 13.3 mmol) was added to a solution of 1-benzyl-7-methoxy--tetralone (1.77 g, 6.64 mmol), 2-methoxybenzylamine (0.91 g, 6.64 mmol), and acetic acid (0.40 g, 6.64 mmol) in methanol (100 mL). The reaction mixture was stirred for 3 days under nitrogen and then concentrated in vacuo to provide a yellow foam. Saturated aqueous sodium carbonate solution (100 mL) was added to this residue and the resulting mixture was extracted with chloroform. The chloroform extracts were combined, dried ($Na_2SO_4$), and concentrated to provide a red-brown oil which was purified on flash silica gel (1:1 hexanes-chloroform to 1:9 hexanes-chloroform) to provide the desired product as a red-brown oil. This material was dissolved in methanol (300 mL) and 48% hydrobromic acid (0.62 mL) was added. Diethyl ether (800 mL) and hexanes (200 mL) were added and a cream-colored solid precipitated out of solution. This solid was crystallized from methanol to give 1.31 g (42%) of rac-cis-1-(phenylmethyl)-7-methoxy-N-(2-methoxyphenylmethyl)-1,2,3,4-tetrahydro-2-naphthalenamine monohydrobromide 15. mp 262–264.5° C. MS (CI-$CH_4$), m/z 388 ($MH^+$). $^1$H NMR (DMSO-$d_6$) 2.01–2.30 (m, 2H), 2.69–2.92 (m, 1H), 2.96–3.07 (m, 1H), 3.13–3.35 (m, 1H), 3.24 (s, 3H), 3.25–3.48 (br m, 2H), 3.51–3.62 (br m, 1H), 3.85 (s, 3H), 4.36 (AB multiplet, 2H), 6.66 (dd, J=8.4, 2.7 Hz, 1H), 6.98–7.15 (m, 6H), 7.18–7.32 (m, 4H), 7.47 (t, J=7.9 Hz, 1H), 7.53 (d, J=7.3 Hz, 1 H), 8.62–8.82 (br s, 1H), 8.98–9.18 (br s, 1H).

Elemental analysis: Calculated for $C_{26}H_{29}NO \cdot HBr$: C, 66.67; H, 6.46; N, 2.99; Br, 17.06. Found C, 66.51; H, 6.71; N, 2.87; Br, 16.59.

Example 9 rac-trans-1-(4-Fluorophenylmethyl)-N-(2-(3-indolyl)ethyl)-1,2,3,4-tetrahydro-2-naphthalenamine monooxalate (16)

Sodium cyanoborohydride (1.33 g, 21.2 mmol) was added to a solution of 1-(4-fluorobenzyl)-β-tetralone (2.70 g, 10.6 mmol), prepared as described in Example 5, 2-tryptamine (2.70 g, 10.6 mmol), and acetic acid (0.64 g, 10.6 mmol) in methanol (150 mL). The reaction mixture was stirred for 2 days under nitrogen and then concentrated in vacuo to provide an orange-yellow solid. Saturated aqueous potassium carbonate solution (100 mL) was added to this residue and the resulting mixture was extracted with chloroform. The chloroform extracts were combined, dried ($Na_2SO_4$), and concentrated to provide 5.92 g of a red-brown foam which was purified on flash silica gel (1:1 hexanes-chloroform to 2% methanol-chloroform) to provide the trans product as 0.43 g of a reddish-brown foam. This material was dissolved in acetone (10 mL) and oxalic acid (0.13 g) was added. Diethyl ether (100 mL) and hexanes (900 mL) were added and a cream-colored solid precipitated out of solution. This solid was crystallized from acetone and diethyl ether with decolorizing charcoal to give 0.08 g (2%) rac-trans-1-(4-fluorophenylmethyl)-N-(2-(3-indolyl)ethyl)-1,2,3,4-tetrahydro-2-naphthalenamine monooxalate 16 as a fine white powder, mp 220.5–221.5° C. MS (PB-$CH_4$), m/z 399 ($MH^+$). $^1$H NMR (DMSO-$d_6$) 1.93–2.10 (m, 1H), 2.12–2.30 (m, 1H), 2.67–2.98 (m, 6H), 2.97–3.20 (m, 2H), 3.28–3.45 (m, 2H), 7.00 (t, J=7.4 Hz, 1H), 7.04–7.23 (m, 8H), 7.20–7.31 (m, 2H), 7.35 (d, J=8.1 Hz, 1H), 7.45 (d, J=7.8 Hz, 1H), 8.10–9.05 (brs, 1H).

Elemental analysis: Calculated for $C_{27}H_{27}FN_2 \cdot C_2H_2O_4$: C, 71.30; H, 5.98; N, 5.73; F, 3.89. Found C, 71.01; H, 5.89; N, 5.58; F, 4.04.

Example 10 rac-cis-1-(Phenylmethyl)-N-(2-methoxyphenyl-2-oxomethyl)-1,2,3,4-tetrahydro-2-naphthalenamine monohydrobromide (17)

A. Sodium cyanoborohydride (1.00 g, 15.9 mmol) was added to a suspension of 1-benzyl-tetralone (1.88 g, 7.96 mmol) and ammonium acetate (3.07 g, 39.8 mmol) in methanol (100 mL) under nitrogen. After 5 days of stirring, the reaction mixture was concentrated to provide a beige foam. Saturated aqueous sodium carbonate solution (100 mL) was added to this material and the resulting mixture was extracted with chloroform. The chloroform extracts were combined, dried ($Na_2SO_4$), and concentrated to provide a dark green oil. 1N Hydrochloric acid solution (50 mL) and chloroform (50 mL) were added to this material. A considerable amount of solid remained undissolved so the mixture was partially concentrated in vacuo. The resulting suspension was filtered, and the collected solid was washed with diethyl ether. The filtrate, consisting of diethyl ether and 1N hydrochloric acid solution was poured into a separatory funnel, and the layers were separated. The aqueous acid solution was made basic by the addition of solid potassium carbonate and then extracted with chloroform. The chloroform extracts were combined, dried ($Na_2SO_4$), and concentrated to provide 1.44 g (76%) of 2-amino-1-benzyltetralin as a green oil whose spectral features were identical to those of the sample prepared in Example 4.

B. 2-Methoxybenzoyl chloride (1.12 g, 6.57 mmol) was added to an ice-cooled solution of 2-amino-1-benzyltetralin (1.30 g, 5.48 mmol) and triethylamine (1.12 g, 11.0 mmol) in dichloromethane (50 mL). The solution was allowed to slowly warm to ambient temperature. After 3 days of stirring, the reaction mixture was poured into saturated aqueous sodium bicarbonate solution (50 mL). The layers were separated, and the aqueous layer was extracted with chloroform. The organic extracts were combined, dried ($Na_2SO_4$), and concentrated to provide 2.71 g of a golden-brown oil. This material was crystallized from diethyl ether and then was recrystallized twice from diethyl ether (decolorizing charcoal) and finally from diethyl ether and hexanes. A final recrystallization from diethyl ether provided 0.14 g (7%) of rac-cis-1-(phenylmethyl)-N-(2- methoxyphenyl-2-oxomethyl)-1,2,3,4-tetrahydro-2-naphthalenamine monohydrobromide 17 as snow-white needles. mp 132–134° C. MS (PB-CH$_4$), m/z 372 (MH$^+$). $^1$H NMR (DMSO-d$_6$) 1.92–2.03 (m, 1H), 2.05–2.16 (m, 1H), 2.89–2.99 (m, 3H), 3.13 (dd, J=13.5, 6.8 Hz, 1H), 3.31–3.42 (m, 1H), 3.66 (s, 3H), 4.49–4.59 (m, 1H), 6.91 (d, J=8.2 Hz, 1H), 7.02–7.32 (m, 10H), 7.43 (td, J=15.6, 1.9 Hz, 1H), 7.93 (br d, J=7.5Hz, 1H), 8.21 (dd, J=7.7, 1.8 Hz, 1 H).

Elemental analysis: Calculated for C$_{25}$H$_{25}$NO$_2$: C, 80.83; H, 6.78; N, 3.77. Found C, 80.75; H, 6.69; N, 3.12.

Example 11 rac-cis-1-(Phenylmethyl)-7-methoxy-N-(2-(3-indolyl) ethyl)-1,2,3,4-tetrahydro-2-naphthalenamine 0.8 fumarate 0.8 methanol 0.2 hydrate (18)

Sodium cyanoborohydride (0.85 g, 13.7 mmol) was added to a solution of 1-benzyl-7-methoxy--tetralone (1.82 g, 6.83 mmol), prepared as described in Example 7, 2-tryptamine (1.09 g, 6.83 mmol), and acetic acid (0.41 g, 6.83 mmol) in methanol (100 mL). The reaction mixture was stirred for 4 days under nitrogen and then concentrated in vacuo to provide an orange-yellow solid. Saturated aqueous potassium carbonate solution (100 mL) was added to this residue and the resulting mixture was extracted with chloroform. The chloroform extracts were combined, dried (Na$_2$SO$_4$), and concentrated to provide 3.23 g of a red-brown foam which was purified on flash silica gel (1:1 hexanes-chloroform to 2% methanol-chloroform) to provide 1.81 g of a rose-beige foam. This material was dissolved in acetone (150 mL) and fumaric acid (0.51 g) was added. Diethyl ether (500 mL) and hexanes (300 mL) were added and a cream-colored solid precipitated out of solution. This solid was crystallized from methanol with decolorizing charcoal to give 1.09 g (30%) of rac-cis-1-(phenylmethyl)-7-methoxy-N-(2-(3-indolyl)ethyl)-1,2,3,4-tetrahydro-2-naphthalenamine 0.8 fumarate 0.8 methanol 0.2 hydrate 18 as a sparkly white powder. mp 210–215.5° C. MS (CI-NH$_3$), m/z 411 (MH$^+$). $^1$H NMR (DMSO-d$_6$) 1.82–1.98 (m, 1H), 2.40 (br t, J=10.6 Hz, 1H), 2.68–3.04 (m, 5H), 3.05–3.28 (m, 4H), 3.32 (s, 3H), 5.68 (br d, J=2.5 Hz, 1H), 6.55 (s, 2H), 6.62 (dd, J=8.3, 2.7 Hz, 1 H), 6.92–7.08 (m, 4H), 7.09 (t, J=7.1 Hz, 1H), 7.13–7.28 (m, 4H), 7.35 (d, J=8.0 Hz, 1H), 7.58 (d, J=7.8 Hz, 1 H), 10.89 (s, 1H).

Elemental analysis: Calculated for C$_{28}$H$_{30}$N$_2$O·0.8C$_4$H$_4$O$_4$·0.8MeOH·0.8H$_2$O: C, 72.16; H, 6.96; N, 5.26; Karl Fischer H$_2$O, 0.68. Found C, 72.19; H, 6.87; N, 5.17; Karl Fischer H$_2$O, 1.15.

Example 12 rac-trans-1-(Phenylmethyl)-7-methoxy-N-(2(3-indolyl) ethyl)-1,2,3,4-tetrahydro-2-naphthalenamine monooxalate (19)

From the chromatography described in Example 11, trans 1-(phenylmethyl)-7-methoxy-N-(2(3-indolyl)ethyl)-1,2,3,4-tetrahydro-2-naphthalenamine was isolated as 0.46 g of a rose film. This material was dissolved in acetone (10 mL) and oxalic acid (0.15 g) was added. Diethyl ether (300 mL) and hexanes (200 mL) were added to precipitate a beige solid. This material was crystallized from methanol and diethyl ether with decolorizing charcoal to give 0.12 g (4%) of rac-trans-1-(phenylmethyl)-7-methoxy-N-(2(3-indolyl) ethyl)-1,2,3,4-tetrahydro-2-naphthalenamine monooxalate 19 as a snow-white powder. mp 215.5–216.5° C. MS (CI-NH$_3$), m/z 411 (MH$^+$). $^1$H NMR (DMSO-d$_6$) 1.92–2.08 (m, 1H), 2.10–2.30 (m, 1H), 2.66–2.78 (br d, 2H), 2.77–2.92 (m, 3H), 2.92–3.18 (m, 3H), 3.22–3.43 (br m, 2H), 3.65 (s, 3H), 6.67 (d, J=2.5 Hz, 1 H), 6.79 (dd, J=8.4, 2.5 Hz, 1 H), 7.00 (t, J=7.5 Hz, 1H), 7.03–7.12 (m, 3H), 7.19–7.39 (m, 6H), 7.45 (d, J=7.8 Hz, 1 H), 8.22–8.79 (br s, 1H).

Elemental analysis: Calculated for C$_{28}$H$_{30}$N$_2$O·C$_2$H$_2$O$_4$: C, 71.98; H, 6.44; N, 5.60. Found C, 71.69; H, 6.93; N, 5.54.

Example 13 rac-cis-1-(2-Naphthylmethyl)-N-(2-(3-indolyl)ethyl)-1,2,3,4-tetrahydro-2-naphthalenamine hemifumarate methanol (20)

A. A solution of -tetralone (10.0 g, 68.4 mmol) and pyrrolidine (7.98 g, 112 mmol) in benzene (200 mL) was heated in a round bottom flask fitted with a condenser and Dean-Stark trap. After 20 h of heating at reflux, the reaction mixture was cooled and concentrated to provide the enamine as a cream-colored solid. This material was used in the next step without purification.

B. 2-Naphthylmethyl bromide (24.2 g, 109 mmol) was added to a solution of the enamine in acetonitrile (200 mL) which had been dried over 4A molecular sieves. This mixture was heated at reflux under nitrogen for 20 h. After cooling, the reaction mixture was concentrated in vacuo to provide an orange foam. Chloroform (25 mL), glacial acetic acid (50 mL), and water (200 mL), were added to this material and the resulting mixture was stirred at ambient temperature for 20 h. Additional chloroform (200 mL) was added to the reaction mixture and the layers were separated. The organic layer was washed with water, dried (Na$_2$SO$_4$), and concentrated to give 31.13 g of a red-brown oil. This material was purified on a Waters Delta Prep 300 LC apparatus using 4:1 hexanes-dichloromethane to 1:1 hexanes-dichloromethane to yield 16.22 g (83%) of the pure 1-(2-naphthyl)--tetralone product as an orange-yellow oil. $^1$H NMR (CDCl$_3$) 2.40–2.68 (m, 3H), 2.75–2.88 (m 1H), 3.36 (d, J=6.3 Hz, 2H), 3.82 (t, J=6.3 Hz, 1H), 6.92 (d, 7.4 Hz, 1H), 7.02 (d, J=8.3 Hz, 1H), 7.05– 7.22 (m, 3H), 7.33 (s, 1H), 7.35–7.47 (m, 2H), 7.64 (d, J=8.1 Hz, 2H), 7.70–7.81 (m, 1H). MS (FAB), m/z 287 (MH$^+$).

C. Sodium cyanoborohydride (1.44 g, 22.9 mmol) was added to a solution of 1-(2-naphthyl)--tetralone (3.28 g, 11.5 mmol) prepared as described above, 2-tryptamine (1.84 g, 11.5 mmol), and acetic acid (0.69 g, 11.5 mmol) in methanol (150 mL). The reaction mixture was stirred for 22 hours under nitrogen and then concentrated in vacuo to yield an orange-red foam. Saturated aqueous potassium carbonate solution (150 mL) was added to this residue and the resulting mixture was extracted with chloroform. The chloroform extracts were combined, dried (Na$_2$SO$_4$), and concentrated to yield 3.23 g of a red-brown foam which was purified on flash silica gel (1:1 hexanes-chloroform to 2% methanol-chloroform) to yield 2.91 g of a red-brown foam. This material was dissolved in acetone (20 mL) and fumaric acid (0.78 g) was added. Diethyl ether (200 mL) and hexanes (800 mL) were added and a pale pink solid precipitated. This solid was collected and crystallized from methanol and acetone with decolorizing charcoal to give 0.51 g (9%) of rac-cis-1-(2-naphthylmethyl)-N-(2-(3-indolyl)ethyl)-1,2,3,4-tetrahydro-2-naphthalenamine hemifumarate methanol 20 as a white powder. mp 188.5–189.5° C. MS (C-NH$_3$), m/z 431 (MH$^+$). $^1$H NMR (DMSO-d$_6$) 1.80–2.02 (m, 2H), 2.63 (dd, J=12.4, 9.4 Hz, 1H), 2.76–3.04 (m, 7H), 3.25–3.45 (m, 2H), 6.27 (d, J=7.6 Hz, 1 H), 6.55 (s, 1H), 6.74 (t, J=6.7 Hz, 1H), 6.93–7.13 (m, 4H), 7.15–7.28 (m, 2H), 7.35 (d, J=8.0 Hz, 1H), 7.39–7.49 (m, 3H), 7.55 (d, J=7.8 Hz, 1H), 7.63–7.72 (m, 1H), 7.77 (d, J=8.4 Hz, 1H), 7.80–7.90 (m, 1H), 10.83 (s, 1H).

Elemental analysis: Calculated for C$_{31}$H$_{30}$N$_2$·0.5C$_4$H$_4$O$_4$·MeOH: C, 78.43; H, 6.97; N, 5.38. Found C, 78.08; H, 6.66; N, 5.42.

Example 14 rac-trans-1-(2-Naphthylmethyl)-N-(2-(3-indolyl)ethyl)-1,2,3,4-tetrahydro-2-naphthalenamine monooxalate (21)

From the chromatography described in Example 13, the trans product was isolated as a beige foam weighing 0.51 g. This material was dissolved in acetone (20 mL) and oxalic acid (0.15 g) was added. Diethyl ether (20 mL) and hexanes (450 mL) were added to precipitate a cream-colored solid. This material was collected and crystallized from methanol and diethyl ether to give 0.23 g (3.8%) of rac-trans-1-(2-naphthylmethyl)-N-(2-(3-indolyl)ethyl)-1,2,3,4-tetrahydro-2-naphthalenamine monooxalate 21 as a snow-white powder, mp 220.5–222.5° C. MS (PB-NH$_3$), m/z 431 (MH$^+$). $^1$H NMR (DMSO-d$_6$) 1.98–2.12 (m, 1H), 2.17–2.38 (m, 1H), 2.70–2.91 (m, 3H), 2.92–3.22 (m, 3H), 3.25–3.85 (m, 4H), 6.95 (t, J=7.4 Hz, 1H), 6.98–7.13 (m, 2H), 7.10–7.28 (m, 4H), 7.35 (t, J=8.8 Hz, 2H), 7.39–7.52 (m, 3H), 7.75 (s, 1H), 7.79–7.92 (m, 3H), 8.32–8.45 (br s, 1H), 8.45–8.67 (br s, 1H), 10.83 (s, 1H).

Elemental analysis: Calculated for $C_{31}H_{30}N_2 \cdot C_2H_2O_4$: C, 76.13; H, 6.20; N, 5.38. Found C, 75.75; H, 6.10; N, 5.23.

Example 15 rac-cis-1-(2-Naphthylmethyl)-N-(2-methoxyphenylmethyl)-1,2,3,4-tetrahydro-2-naphthalenamine monohydrobromide (22)

Sodium cyanoborohydride (1.40 g, 22.2 mmol) was added to a solution of 1-(2-naphthylmethyl)--tetralone (3.18 g, 11.1 mmol), prepared as described in Example 13, 2-methoxybenzylamine (1.52 g, 11.1 mmol), and acetic acid (0.67 g, 11.1 mmol) in methanol (150 mL). The reaction mixture was stirred for 22 h under nitrogen and was then concentrated in vacuo to yield a yellow-orange foam. Saturated aqueous potassium carbonate solution (100 mL) was added to this residue and the resulting mixture was extracted with chloroform. The chloroform extracts were combined, dried (Na$_2$SO$_4$), and concentrated to yield 4.70 g of a brown foam which was purified on flash silica gel (1:1 hexanes-chloroform to 2% methanol-chloroform) to provide 1.31 g of pure cis-1-(2-naphthylmethyl)-N-(2-methoxyphenylmethyl)-1,2,3,4-tetrahydro-2-naphthalenamine as a golden-brown oil. This material was dissolved in a minimum amount of methanol, and 48% hydrobromic acid (0.36 mL). Diethyl ether and hexanes were added and a white precipitate came out of solution. An additional 1.72 g of the slightly less pure aminotetralin was isolated as a light brown foam. This material was dissolved in methanol (10 mL), and 48% hydrobromic acid (0.47 mL) was added. Diethyl ether (700 mL) and hexanes (300 mL) were added and a light yellow solid precipitated out of solution. The salts formed from each batch of aminotetralin, identical by TLC, were combined and recrystallized from methanol to provide 1.09 g (30%) of rac-cis-1-(2-naphthylmethyl)-N-(2-methoxyphenylmethyl)-1,2,3,4-tetrahydro-2-naphthalenamine monohydrobromide 22 as fine white crystals. mp 237–248° C. MS (CI-NH$_3$), m/z 408 (MH$^+$). $^1$H NMR (DMSO-d$_6$) 2.15–2.37 (br m, 2H), 2.67 (t, J=12.3 Hz, 1H), 2.88–3.05 (m, 1H), 3.09–3.22 (m, 1H), 3.32–3.45 (m, 1H), 3.57–3.72 (m, 2H), 3.85 (s, 3H), 4.43 (AB multiplet, 2H), 5.94 (d, J=7.6 Hz, 1 H), 6.63 (t, J=7.3 Hz, 1H), 7.00–7.11 (m, 2H), 7.15 (d, J=8.8 Hz, 2H), 7.37 (dd, J=8.5, 1.3 Hz, 1H), 7.40–7.52 (m, 4H), 7.57 (dd, J=7.4, 1.1 Hz, 1H), 7.71–7.81 (m, 1H), 7.83–7.93 (m, 2H), 8.85 (br s, 1H), 9.14 (br s, 1H).

Elemental analysis: Calculated for $C_{29}H_{29}NO \cdot HBr$: C, 71.31; H, 6.19; N, 2.87; Br, 16.36. Found C, 71.01; H, 6.25; N, 2.88; Br, 16.29.

Example 16 rac-cis-1-(Phenylmethyl)-N-(2-methoxyphenyl-2-oxoethyl)-1,2,3,4-tetrahydro-2-naphthalenamine (23)

A solution of DCC (2.96 g, 14.4 mmol) in DMF (50 mL) was added dropwise to a solution of 2-amino-1-benzyltetralin (3.10 g, 13.1 mmol), prepared as described in Example 10, 2-methoxyphenylacetic acid (2.17 g, 13.1 mmol) and 1-HOBT (3.53 g, 26.1 mmol) in DMF (150 mL). After 7 days of stirring, water (200 mL) was added to the reaction mixture. The resulting mixture was extracted with ethyl acetate. The ethyl acetate extracts were combined, washed with water, (MgSO$_4$), and concentrated to provide 7.76 g of a brown semisolid. This material was dissolved in ethyl acetate (200 mL) and the resulting solution was washed with aqueous ammonium hydroxide solution, dried (MgSO$_4$), and concentrated to yield 5.24 g of a brown solid which was purified on flash silica gel (1:1 hexanes-chloroform) to provide 2.69 g of a brown solid. This material was recrystallized from acetone (decolorizing charcoal) and hexanes to give 1.00 g (20%) rac-cis-1-(phenylmethyl)-N-(2-methoxyphenyl-2-oxoethyl)-1,2,3,4-tetrahydro-2-naphthalenamine 23 as a white powder, mp 144–145° C. MS (PB-CH$_4$), m/z 386 (MH$^+$). $^1$H NMR (CDCl$_3$) 1.68–1.80 (m, 1H), 1.80–1.93 (m, 1H), 2.50 (dd, J=13.4, 7.6 Hz, 1H), 2.72–2.82 (m, 1H), 2.90 (dd, J=13.3, 6.8 Hz, 1H), 3.17–3.24 (m, 1H), 3.52 (AB quartet, J=14.3 Hz, 2H), 3.56 (s, 3H), 4.09–4.19 (m, 1H), 6.02 (br d, J=8.0 Hz, 1H), 6.78–6.99 (m, 5H), 7.00–7.30 (m, 8H).

Elemental analysis: Calculated for $C_{26}H_{27}NO_2$: C, 81.01; H, 7.06; N, 3.63. Found C, 80.92; H, 6.89; N, 3.50.

Example 17 rac-cis-1-(4-Fluorophenylmethyl)-N-(3-phenylpropyl)-1,2,3,4-tetrahydro-2-naphthalenamine monohydrobromide (24)

Sodium cyanoborohydride (1.63 g, 26 mmol) was added to a solution of 1-(4-fluorobenzyl)--tetralone (3.30 g, 13.0 mmol), prepared as described in Example 5, 3-phenylpropylamine (1.75 g, 13.0 mmol), and acetic acid (0.78 g, 13.0 mmol) in methanol (200 mL). The reaction mixture was stirred for 3 days under nitrogen and then concentrated in vacuo to yield an orange foam. Saturated aqueous sodium carbonate solution was added to this residue and the resulting mixture was extracted with chloroform. The chloroform extracts were combined, dried (Na$_2$SO$_4$), and concentrated to provide an orange-brown foam which was purified on flash silica gel (1:1 hexanes-chloroform) to provide pure product as 1.60 g of a brown oil as well as 1.40 g of less pure product as a brown oil. The pure product was dissolved in methanol, and 48% hydrobromic acid (0.48 mL) was added. Diethyl ether was added which caused a beige solid to precipitate. The slightly less pure product was dissolved in a minimum amount of methanol (75 mL), and 48% hydrobromic acid (0.42 mL) was added. Diethyl ether (500 mL) and hexanes (500 mL) were added and a white solid precipitated out of solution. These materials were independently collected and shown to be identical by TLC. The solids were combined and crystallized from methanol and diethyl ether to give 1.90 g (32%) of rac-cis-1-(4-fluorophenylmethyl)-N-(3-phenylpropyl)-1,2,3,4-tetrahydro-2-naphthalenamine monohydrobromide 24 as sparkling white crystals, mp 241–245° C. MS (PB-NH$_3$), m/z 374 (MH$^+$). $^1$H NMR (DMSO-d$_6$) 1.94–2.22 (m, 4H), 2.72 (t, 2H), 2.82–3.40 (m, 7H), 3.52–3.65 (br m, 1H), 5.93 (d, 1H), 6.75 (t, 1H), 6.92–7.16 (m, 6H), 7.18–7.38 (m, 5H), 8.50–8.93 (br m, 2H).

Elemental analysis: Calculated for $C_{26}H_{28}FN \cdot HBr$: C, 68.72; H, 6.43; N, 3.00; Br, 17.58; F, 4.18. Found C, 68.94; H, 6.44; N, 3.02; Br, 17.44; F, 4.17.

Example 18 rac-cis-1-(3-pyridylmethyl)-N-(2-(3,4-dimethoxyphenyl)ethyl-1,2,3,4-tetrahydro-2-naphthalenamine monohydrobromide (28)

A. Tetralone (25.0 g, 171.0 mmol) was placed in a 1L round bottom flask followed by benzene (650 mL). 3-Pyridine carboxaldehyde (14.5 mL, 153.9 mmol) was added to this stirred solution followed by piperidine (0.423 mL, 4.28 mmol). The reaction vessel was flushed with nitrogen and a Dean-Stark trap equipped with a reflux condenser was installed. The reaction mixture was heated at reflux overnight, then cooled and the benzene was removed in vacuo. This material was purified via silica gel chromatography eluting with a gradient of 100% hexanes to 40% hexanes/60% ethyl acetate. After collecting and concentrating the fractions, 1-(3-pyridylmethyilidenyl)--tetralone 25 was obtained as a yellow waxy solid (30.8 g, 130.9 mmol). MS: M+1=236.

B. The tetralone 25 from the previous reaction (30.8 g, 130.9 mmol) was dissolved in methanol (650 mL) with stirring. Ammonium acetate (151.3 g, 1964 mmol) and sodium cyanoborohydride (41.1 g, 654 mmol) were added. The reaction vessel was flushed with nitrogen and a reflux condenser was installed. The reaction mixture was heated at reflux overnight. The solvent was removed in vacuo to give the crude product. This was dissolved in methylene chloride (600 mL) and water (300 mL). 1N Sodium hydroxide solution (1500 mL) was added to this biphasic mixture. The aqueous layer was removed and the organic layer was subsequently washed several times with dilute sodium hydroxide solution. The combined aqueous washes were extracted with fresh methylene chloride. The combined organic extracts were dried over sodium sulfate, filtered, and the solvent removed in vacuo. The resulting residue was dissolved in ethyl ether and an excess of 1N hydrogen chloride in ethyl ether was added to precipitate the product. This material was triturated with additional portions of ethyl ether and filtered. The material was dried under vacuum. The -picolylmethyl--aminotetralin bis-hydrochloride 26 was obtained as a hygroscopic greenish powder (26.0 g, 83.5 mmol). MS: M+1=239; NMR($d_6$-DMSO): 8.71 (br, 3H), 8.62 (d, 1H), 8.47 (s, 1H), 7.97 (d, 1H), 7.63 (dd, 1H), 7.24–7.08 (m, 2H), 6.83 (dd, 1H), 6.03 (d, 1H), 3.68–3.52 (m, 1H), 3.44–3.35 (m, 2H), 3.12–2.83 (m, 2H), 2.71–2.58 (t app., 1H), 2.21–1.97 (m, 2H)

C. The -picolylmethyl--aminotetralin bis-hydrochloride 26 (0.210 g, 0.672 mmol) was put into a 10 mL round bottom flask and dimethylformamide (7 mL) was added. With stirring, diisopropylethylamine (0.387 mL, 2.22 mmol) was added followed by 3,4-dimethoxyphenylacetyl chloride (0.144 g, 0.672 mmol). The reaction was flushed with nitrogen, capped and stirred overnight. The contents of the reaction vessel were transferred to water (70 mL) in an Erlenmeyer flask which resulted in the formation of a milky precipitate. This aqueous solution was extracted three times with methylene chloride and the combined organics were washed seven times with water to remove the dimethylformamide. The organic materials were dried over sodium sulfate, filtered, and the solvents were removed in vacuo. The resultant moist material was thoroughly dried under vacuum to yield the corresponding amide product 27 (0.262 g, 0.629 mmol). MS: M+1=417

D. The amide 27 from the previous reaction (0.262 g, 0.629 mmol) was put into a 100 mL round bottom flask and dissolved in tetrahydrofuran (25 mL). Borane-tetrahydrofuran complex (6.3 mL, 6.3 mmol, 1 M in THF) was added to this solution. The reaction vessel was flushed with nitrogen, a reflux condenser was installed and the reaction mixture was heated at reflux for 1 hour. The reaction was then cooled and water (7 mL) was carefully added. The quenched reaction was allowed to stand overnight. The tetrahydrofuran was removed in vacuo; hydrogen chloride (25 mL of a 1N solution) was added and this mixture was heated at reflux for 30 minutes. The reaction was made basic via the addition of sodium hydroxide (1N solution) which resulted in the formation of a milky precipitate. This aqueous solution was extracted three times with methylene chloride. The combined organics were dried over sodium sulfate, filtered, and the solvent removed in vacuo. The resulting residue was dissolved in methanol (5 mL) and an excess of 1N hydrogen chloride in ethyl ether was added. The solvents were removed in vacuo and the resulting residue was triturated with ethyl ether, followed by filtration to isolate rac-cis-1-(3-pyridylmethyl)-N-(2-(3,4-dimethoxyphenyl)ethyl-1,2,3,4-tetrahydro-2-naphthalenamine monohydrobromide 28 (0.125 g, 0.262 mmol) (FIG. 7). MS: M+1=403; NMR($d_6$-DMSO): 9.94–9.75 (br, 1H), 9.61–9.40 (br, 1H), 8.79 (d, 1H), 8.73 (s, 1H), 8.32 (d, 1H), 7.92 (dd, 1H), 7.24–7.05 (m, 3H), 6.96–6.73 (m, 3H), 5.95 (d, 1H), 3.81–3.68 (m, 6H), 3.67–3.47 (m, 3H), 3.46–3.23 (m, 2H), 3.22–3.01 (m, 3H), 3.00–2.63 (m, 3H), 2.39–2.13 (m, 1H).

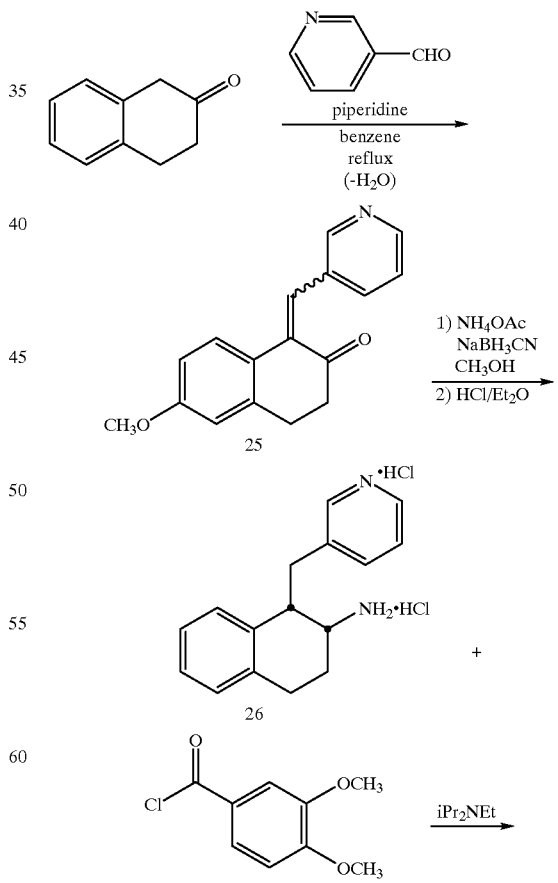

FIG. 7

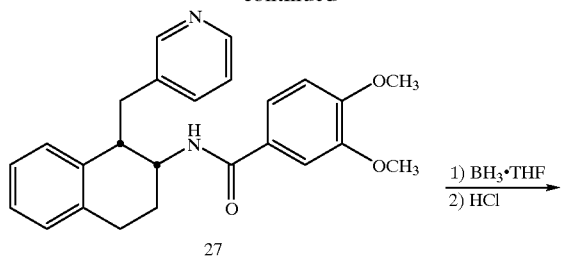

IN VITRO ASSAYS

NPY5 HTS Centrifugation Assay

The compounds described in this invention were evaluated for binding to the human neuropeptide Y5 receptor.

Stable Transfection

The human NPY5 receptor cDNA (Genbank Accession number U66275) was inserted into the vector pCIneo (Invitrogen) and transfected into human embryonic kidney cells (HEK-293) via Calcium phosphate method (Cullen 1987). Stably transfected cells were selected with G-418 (600 μg/mL). Stably transfected cells served as the source for the membranes for the NPY5 receptor binding assay.

Membrane Preparation

NPY5-transfected HEK293 cells were grown to confluence in 150 cm² culture dishes. Cells were washed once with phosphate-buffered saline (Gibco Cat# 14040-133). Cells were then incubated in phosphate-buffered saline without Calcium and without Magnesium, supplemented with 2 mM EDTA. Cells were incubated for 10 minutes at room temperature and the cells were collected by repetitive pipeting. Cells were formed into pellets and then frozen at −80° C. until needed. Frozen pellets were homogenized with a polytron at full speed for 12 seconds in a homogenization buffer (20 mM Tris HCl, 5 mM EDTA, pH 7.4). Homogenates were centrifuged for 5 minutes at 4° C. at 200 g. Supernatants were transferred to corex tubes and centrifuged for 25 minutes at 28,000 g. Pellets were re-suspended in Binding (20 mM HEPES, 10 mM NaCl, 0.22 mM $KH_2PO_4$, 1.3 mM $CaCl_2$, 0.8 mM $MgSO_4$, pH 7.4). Membranes were kept on ice until use.

A competition binding assay, known to those skilled in the art, was used in which aminotetralins (I) compete with $^{125}$I-PYY for binding to cell membranes. In simple terms, the less $^{125}$I-PYY bound to the membranes implies that a compound is a good inhibitor (competitor). Bound $^{125}$I-PYY is determined by centrifugation of membranes, aspirating supernatant, washing away residual $^{125}$I-PYY and subsequently counting the bound sample in a g-counter.

Procedure for Radioligand binding assay

Compounds to be tested were prepared as 10x stocks in binding buffer and added first to assay tubes (RIA vials, Sarstedt). Twenty (20) μL of each 10x compound stock is pipeted into vials and 80 μL of $^{125}$I-PYY (NEN catalog number NEX240), which has been diluted to a concentration of 200 pM in 0.25 % BSA in binding buffer, is added to the compound tubes (final concentration of $^{125}$I-PYY is 80 pM). To each tube is added 100 μL of membranes and the mixture is agitated by pipeting 2 times. Samples are incubated for 1 hr at room temperature. Aluminum cast plates (Sarstedt) containing the vials are then centrifuged 10 minutes at 3200 rpm in a Sorvall RT6000. Supernatant is then aspirated. To each vial 400 μL PBS is added and this is then aspirated again. Vials are then put in carrier polypropylene 12×75 tube and counted in gamma counter (Packard). Non-specific binding is determined in the presence of 300 nM NPY. Percent inhibition of $^{125}$I-PYY binding is calculated by subtracting non-specific binding from the test samples (compound (I)), taking these counts and dividing by total binding, and multiplying by 100.

TABLE 1

Binding Affinities of Compounds (I) for the Human NPY Y5 Receptor
(expressed as % Inhibition of $^{125}$I-PYY Binding)

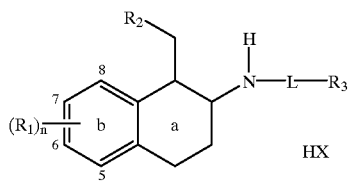

(1)

| # | $R^1$ | ring junction | $R_2$ | L | $R_3$ | % Inh @ 30 uM | % Inh @ 3 uM |
|---|---|---|---|---|---|---|---|
| 6 | 6-OMe | cis | Ph | —$CH_2$—$CH_2$— | (3,4-diOMe)Ph | 101 | 86 |
| 8 | H | cis | Ph | —$CH_2$—$CH_2$— | 3-indolyl | 105 | 73 |
| 9 | H | cis | Ph | —$CH_2$— | (4-F)Ph | 97 | 20 |
| 11 | H | cis | Ph | —$CH_2$— | (2-OMe)Ph | 96 | 21 |
| 12 | H | cis | (4-F)Ph | —$CH_2$— | (2-OMe)Ph | 98 | 16 |
| 13 | H | trans | (4-F)Ph | —$CH_2$— | (2-OMe)Ph | 89 | 16 |
| 14 | H | cis | Ph | —$CH_2$—$CH_2$— | (4-F)Ph | 98 | 13 |
| 15 | 7-OMe | cis | Ph | —$CH_2$— | (2-OMe)Ph | 100 | 31 |

TABLE 1-continued

Binding Affinities of Compounds (I) for the Human NPY Y5 Receptor
(expressed as % Inhibition of $^{125}$I-PYY Binding)

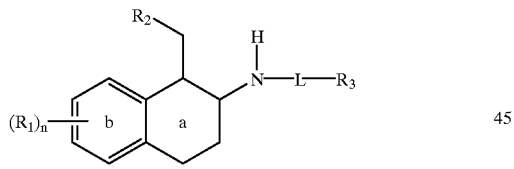

(1)

| # | $R^1$ | ring junction | $R_2$ | L | $R_3$ | % Inh @ 30 uM | % Inh @ 3 uM |
|---|---|---|---|---|---|---|---|
| 16 | H | cis | Ph | —CH$_2$—CH$_2$— | 3-indolyl | 101 | 48 |
| 17 | H | cis | Ph | —C(O)— | (2-OMe)Ph | 98 | 65 |
| 18 | 7-OMe | cis | Ph | —CH$_2$—CH$_2$— | 3-indolyl | 104 | 61 |
| 19 | 7-OMe | trans | Ph | —CH$_2$—CH$_2$— | 3-indolyl | 100 | 49 |
| 20 | H | cis | 2-naphthyl | —CH$_2$—CH$_2$— | 3-indolyl | 99 | 27 |
| 21 | H | trans | 2-naphthyl | —CH$_2$—CH$_2$— | 3-indolyl | 103 | 33 |
| 22 | H | cis | 2-naphthyl | —CH$_2$— | (2-OMe)Ph | 96 | 15 |
| 23 | H | cis | Ph | —C(O)—CH$_2$— | (2-OMe)Ph | 47 | 12 |
| 24 | H | cis | Ph | —(CH$_2$)$_3$— | Ph | 102 | 19 |
| 28 | H | cis | 3-pyridyl | —CH$_2$—CH$_2$— | Ph | 66 | 11 |
| 29 | 6-OMe | cis | Ph | —CH$_2$—CH$_2$— | Ph | 95 | 33 |
| 30 | 6-OMe | cis | Ph | —CH$_2$—CH$_2$— | (4-OMe)Ph | 99 | 62 |
| 31 | 6-OMe | cis | Ph | —CH$_2$—CH$_2$— | (3,4-diCl)Ph | 93 | 31 |
| 32 | 6-OMe | cis | (3-OMe)Ph | —CH$_2$—CH$_2$— | (3,4-diOMe)Ph | 97 | 44 |
| 33 | 6-OMe | cis | 1-naphthyl | —CH$_2$—CH$_2$— | (3,4-diOMe)Ph | 73 | 16 |
| 34 | 6-OMe | cis | (4-OMe)Ph | —CH$_2$—CH$_2$— | (3,4-diOMe)Ph | 103 | 89 |
| 35 | H | cis | Ph | —CH$_2$—CH$_2$— | (3,4-diOMe)Ph | 99 | 47 |
| 36 | 6-OMe | cis | Ph | —CH$_2$—CH$_2$— | (4-OPh)Ph | 87 | 35 |
| 37 | 6-OMe | cis | Ph | —CH$_2$—CH$_2$— | (4-MeO—CH$_2$CH$_2$O—)Ph | ND* | 84 |

*(ND = not determined)

What is claimed is:

1. A compound of formula (I)

(I)

wherein $R_1$ is independently selected from the group consisting of hydroxy; halo; $C_{1-8}$alkoxy; substituted $C_{1-8}$ alkoxy wherein the substituent is selected from halo, selected from the group consisting of chloro, bromo, fluoro and iodo; trifluoroalkyl; $C_{1-8}$alkylthio and substituted $C_{1-8}$alkylthio wherein the substituent is selected from halo, selected from the group consisting of chloro, bromo, fluoro and iodo, trifluoroalkyl and $C_{1-8}$alkoxy; $C_{3-6}$cycloalkyl; $C_{3-8}$cycloalkyloxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$R_2$ is selected from the group consisting of hydrogen; $C_{2-6}$alkenyl; halo, selected from the group consisting of fluoro and chloro; $C_{3-7}$cycloalkyl; phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; naphthyl; phenoxy; substituted phenoxy wherein the substituent is selected from halo, $C_{1-6}$alkyl, $C_{1-6}$alkoxy, trifluoro$C_{1-6}$alkyl, cyano and nitro; phenylthio and substituted phenylthio wherein the substituent is selected from halo, $C_{1-6}$alkyl, nitro and amino; a heteroaryl group selected from the group consisting of pyridyl, pyrimidyl, furyl, thienyl, and imidazolyl; substituted heteroaryl wherein the substitutent is selected from $C_{1-6}$alkyl and halo;

L is selected from the group consisting of $C_{1-8}$alkylene; $C_{2-8}$alkenylene; $C_{2-8}$alkynylene; $C_{1-4}$alkylene$C_{3-8}$cycloalkylene;

$R_3$ is selected from $C_{1-8}$alkyl; substituted $C_{1-8}$alkyl wherein the substituent is selected from alkoxy and halo; alkoxyalkyloxy; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from indolyl, pyridyl, pyrimidyl, furyl, thienyl and imidazolyl; and substituted heteroaryl wherein the substituent is selected from halo, nitro, amino and cyano;

and enantiomers, diastereomers, and pharmaceutically acceptable salts thereof.

2. A compound of claim 1 wherein $R_1$ is halo, alkyl, alkoxy or hydrogen; $R_2$ is alkyl, halo, phenyl, substituted phenyl, heteroaryl or naphthyl; n is 0–2; L is alkylene; and $R_3$ is alkyl, substituted alkyl, phenyl, substituted phenyl, heteroaryl or substituted heteroaryl.

3. A compound of claim 2 wherein the heteroaryl group in $R_2$ is selected from pyridyl, pyrimidyl, furyl, thienyl and imidazolyl.

4. A compound of claim 2 wherein the heteroaryl group in $R_3$ is selected from indolyl, pyridyl, pyrimidyl, furyl, thienyl and imidazolyl.

5. A compound of claim 1 wherein the pharmaceutically acceptable salt is selected from hydrochlorides, hydrobromides, oxalates and trifluoroacetates.

6. A compound of the formula:

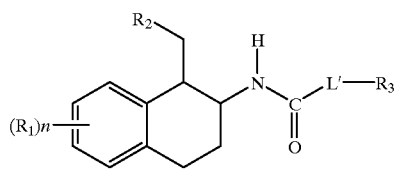

wherein $R_1$ is independently selected from the group consisting of hydrogen; hydroxy; halo; $C_{1-8}$alkyl; $C_{1-8}$alkoxy; substituted $C_{1-8}$alkoxy wherein the substituent is selected from halo, selected from chloro, bromo, fluoro and iodo; trifluoroalkyl; $C_{1-8}$alkylthio and substituted $C_{1-8}$alkylthio wherein the substituent is selected from halo, selected from chloro, bromo, fluoro and iodo, trifluoroalkyl and $C_{1-8}$alkoxy; $C_{3-6}$cycloalkyl; $C_{3-8}$cycloalkyloxy; nitro; amino; $C_{1-6}$alkylamino; $C_{1-8}$dialkylamino; $C_{4-8}$cycloalkylamino; cyano; carboxy; $C_{1-5}$alkoxycarbonyl; $C_{1-5}$alkylcarbonyloxy; formyl; carbamoyl; phenyl; substituted phenyl wherein the substitutent is selected from halo, hydroxyl, nitro, amino and cyano;

n is 0–2

$R_2$ is selected from the group consisting of hydrogen; $C_{1-6}$alkyl; $C_{2-6}$alkenyl; halo, selected from fluoro and chloro; $C_{3-7}$cycloalkyl; phenyl; substituted phenyl wherein the substituent is selected from halo, $C_{1-6}$alkyl, $C_{1-6}$alkoxy, trifluoro$C_{1-6}$alkyl, cyano, nitro, amino, $C_{1-6}$alkylamino, and $C_{1-6}$dialkylamino; naphthyl; phenoxy; substituted phenoxy wherein the substituent is selected from halo, $C_{1-6}$alkyl, $C_{1-6}$alkoxy, trifluoro$C_{1-6}$alkyl, cyano and nitro; phenylthio and substituted phenylthio wherein the substituent is selected from halo, $C_{1-6}$alkyl, nitro and amino; a heteroaryl group selected from pyridyl, pyrimidyl, furyl, thienyl, and imidazolyl; substituted heteroaryl wherein the substitutent is selected from $C_{1-6}$alkyl and halo;

L' is selected from the group consisting of $C_{1-7}$alkylene; $C_{2-7}$alkenylene; $C_{2-7}$alkynylene; $C_{1-3}$alkylene$C_{3-8}$cycloalkylene;

$R_3$ is selected from $C_{1-8}$alkyl; substituted $C_{1-8}$alkyl wherein the substituent is selected from alkoxy and halo; alkoxyalkyloxy; cycloalkyl; substituted cycloalkyl wherein the substituent is selected from alkoxy and halo; phenyl; substituted phenyl wherein the substituent is selected from $C_{1-8}$alkyl, halo, nitro, amino, alkylamino, alkylsulfonyl, alkoxy and cyano; naphthyl; substituted naphthyl wherein the substituent is selected from halo, nitro, amino and cyano; heteroaryl wherein the heteroaryl group is selected from indolyl, pyridyl, pyrimidyl, furyl, thienyl and imidazolyl; and substituted heteroaryl wherein the substituent is selected from halo, nitro, amino and cyano.

7. A compound of claim 1 selected from the group consisting of:

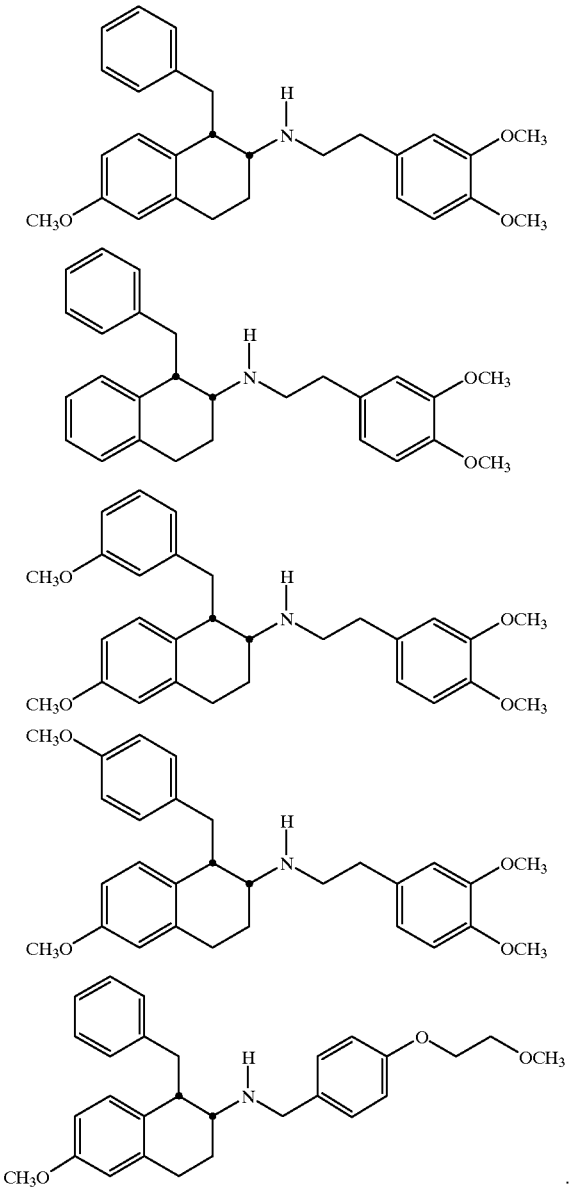

8. A compound of claim 1 selected from the group consisting of:

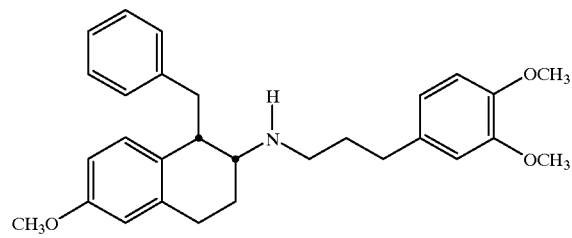

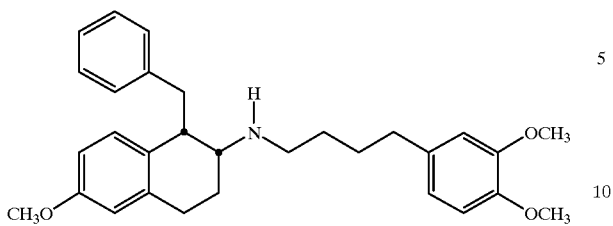

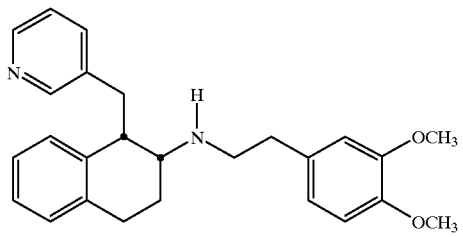

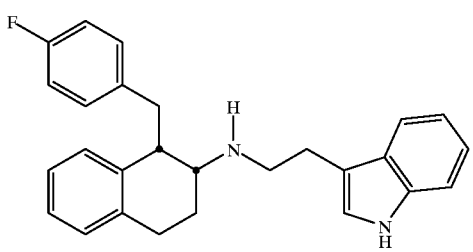

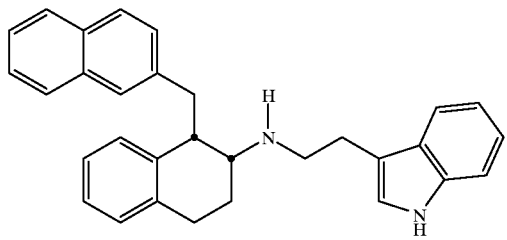

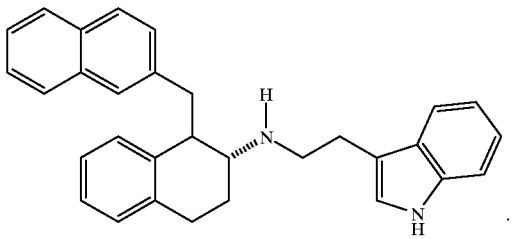

9. A compound of claim 1 selected from the group consisting of:

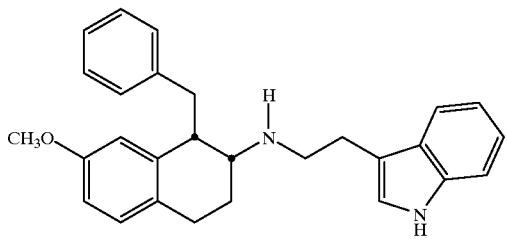

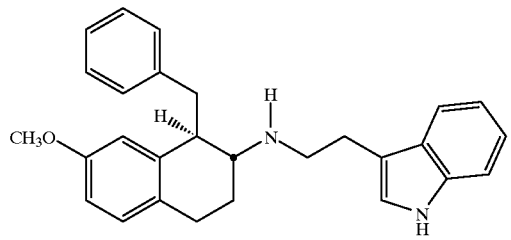

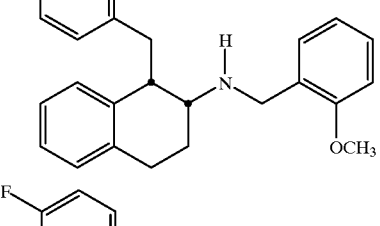

10. A compound of claim 1 selected from the group consisting of:

rac-cis-1-(Phenylmethyl)-6-methoxy-N-(2-(3,4-dimethoxyphenyl)ethyl)-1,2,3,4-tetrahydro-2-naphthalenamine;

rac-cis-1-(Phenylmethyl)-6-methoxy-N-(2-(3-indolyl)ethyl)-1,2,3,4-tetrahydro-2-naphthalenamine hemifumarate;

rac-cis-1-(Phenylmethyl)-N-(4-fluorophenylmethyl)-1,2,3,4-tetrahydro-2-naphthalenamine monohydrobromide;

rac-cis-1-(Phenylmethyl)-N-(2-methoxyphenylmethyl)-1,2,3,4-tetrahydro-2-naphthalenamine;

rac-cis-1-(Phenylmethyl)-N-(2-methoxyphenylmethyl)-1,2,3,4-tetrahydro-2-naphthalenamine monohydrobromide; and rac-cis-1-(4-Fluorophenylmethyl)-N-(2-methoxyphenylmethyl)-1,2,3,4-tetrahydro-2-naphthalenamine monohydrobromide.

11. A compound of claim 1 selected from the group consisting of:

rac-trans-1-(4-Fluorophenylmethyl)-N-(2-methoxyphenylmethyl)-1,2,3,4-tetrahydro-2-naphthalenamine monooxalate;

rac-cis-1-(Phenylmethyl)-N-(4-fluorophenylmethyl)-1,2,3,4-tetrahydro-2-naphthalenamine monohydrobromide;

rac-cis-1-(Phenylmethyl)-7-methoxy-N-(2-methoxyphenylmethyl)-1,2,3,4-tetrahydro-2-naphthalenamine monohydrobromide;

rac-trans-1-(4-Fluorophenylmethyl)-N-(2-(3-indolyl)ethyl)-1,2,3,4-tetrahydro-2-naphthalenamine monooxalate;

rac-cis-1-(Phenylmethyl)-N-(2-methoxyphenyl-2-oxomethyl)-1,2,3,4-tetrahydro-2-naphthalenamine monohydrobromide; and rac-cis-1-(Phenylmethyl)-7-methoxy-N-(2-(3-indolyl)ethyl)-1,2,3,4-tetrahydro-2-naphthalenamine 0.8 fumarate 0.8 methanol 0.2 hydrate.

12. A compound of claim 1 selected from the group consisting of:

rac-trans-1-(Phenylmethyl)-7-methoxy-N-(2(3-indolyl)ethyl)-1,2,3,4-tetrahydro-2-naphthalenamine monooxalate;

rac-cis-1-(2-Naphthylmethyl)-N-(2-(3-indolyl)ethyl)-1,2,3,4-tetrahydro-2-naphthalenamine hemifumarate methanol;

rac-trans-1-(2-Naphthylmethyl)-N-(2-(3-indolyl)ethyl)-1,2,3,4-tetrahydro-2-naphthalenamine monooxalate;

rac-cis-1-(2-Naphthylmethyl)-N-(2-methoxyphenylmethyl)-1,2,3,4-tetrahydro-2-naphthalenamine monohydrobromide; and rac-cis-1-(Phenylmethyl)-N-(2-methoxyphenyl-2-oxoethyl)-1,2,3,4-tetrahydro-2-naphthalenamine.

13. A compound of claim 1 selected from the group consisting of:

rac-cis-1-(4-Fluorophenylmethyl)-N-(3-phenylpropyl)-1,2,3,4-tetrahydro-2-naphthalenamine monohydrobromide; and rac-cis-1-(3-pyridylmethyl)-N-(2-(3,4-dimethoxyphenyl)ethyl-1,2,3,4-tetrahydro-2-naphthalenamine monohydrobromide.

14. A method of treating disorders and diseases associated with NPY receptor subtype Y5 comprising administering to a mammal in need of such treatment a therapeutically effective amount of a compound of claim 1.

15. A pharmaceutical composition for the treatment of diseases or disorders associated with NPY Y5 receptor subtype comprising a therapeutically effective amount of a compound of claim 1 and a pharmaceutically acceptable carrier.

16. A pharmaceutical composition according to claim 12 for the treatment of disorders or disease states caused by eating disorders, obesity, bulimia nervosa, diabetes, dyspilipidimia, hypertension, memory loss, epileptic seizures, migraine, sleep disturbances, pain, sexual/reproductive disorders, depression, anxiety, cerebral hemorrhage, shock, congestive heart failure, nasal congestion or diarrhea.

* * * * *

UNITED STATES PATENT AND TRADEMARK OFFICE
CERTIFICATE OF CORRECTION

PATENT NO. : 6,201,025 B1
DATED : March 13, 2001
INVENTOR(S) : Scott Dax et al.

It is certified that error appears in the above-identified patent and that said Letters Patent is hereby corrected as shown below:

<u>Column 33,</u>
Line 50, after "consisting of" add -- $C_{1-8}$alkyl --.
Line 51, add -- hydrogen -- before "hydroxy".
Line 66, delete "hydrogen".

<u>Column 35,</u>
Line 2, delete "alkyl".

Signed and Sealed this

First Day of June, 2004

JON W. DUDAS
*Acting Director of the United States Patent and Trademark Office*